United States Patent [19]
Cruz et al.

[11] Patent Number: 5,889,147
[45] Date of Patent: Mar. 30, 1999

[54] BROMO-TRYPTOPHAN CONOPEPTIDES

[75] Inventors: Lourdes J. Cruz; Baldomero M. Olivera; J. Michael McIntosh, all of Salt Lake City, Utah; Elsie Jimenez, Quezon, Philippines; A. Grey Craig, Solana Beach, Calif.; Jean A. Rivier, La Jolla, Calif.; David Julius, San Francisco, Calif.; Laura England, Alameda, Calif.

[73] Assignees: University of Utah Research Foundation, Salt Lake City, Utah; Salk Institute, La Jolla; Regents of the University of California, Oakland, both of Calif.

[21] Appl. No.: 785,534

[22] Filed: Jan. 17, 1997

[51] Int. Cl.⁶ .......................... A61K 38/08; A61K 38/10; A61K 38/16; C07K 7/04
[52] U.S. Cl. .......................... 530/324; 530/325; 530/326; 530/327; 530/328
[58] Field of Search ..................................... 530/324, 327, 530/328, 325–326

[56] References Cited

U.S. PATENT DOCUMENTS

| | | | |
|---|---|---|---|
| 4,224,199 | 9/1980 | Meyers | 260/8 |
| 5,064,939 | 11/1991 | Rivier | 530/317 |
| 5,371,070 | 12/1994 | Koerber | 514/9 |
| 5,750,499 | 5/1998 | Hoeger | 514/9 |

FOREIGN PATENT DOCUMENTS 2021121  5/1978  United Kingdom .

*Primary Examiner*—Cecilia J. Tsang
*Assistant Examiner*—Michael Borin
*Attorney, Agent, or Firm*—Rothwell, Figg, Ernst & Kurz, P.C.

[57] ABSTRACT

The present invention is directed to conopeptides having 6–45 amino acids, including one or more bromo-tryptophan residues. More specifically, the present invention is directed to conopeptides having the general formula: $R-(Cys)_n-R^1-B-R^2-Cys-R^3$, wherein R is a peptide chain of 0–24 amino acids, $R^1$ is a peptide chain of 0 to 31 amino acids, $R^2$ is a peptide chain of 0–29 amino acids, $R^3$ is a peptide chain of 0 to 26 amino acids, B is 6-bromo-tryptophan, n is 0 or 1 and the total length of the conopeptide is from about 6 to about 45 amino acids. The invention also includes pharmaceutically acceptable salts of the conopeptides. These bromo-tryptophan containing conopeptides invention are useful as antihelminthic agents, anti-vomiting agents, sleep-inducing agents, adjuncts to anesthesia, anticonvulsant or neuroprotective agents.

16 Claims, No Drawings

BROMO-TRYPTOPHAN CONOPEPTIDES

This invention was made with Government support under Grant Nos. GM48677, MH53631 and K20 MH00929 awarded by the National Institutes of Health, Bethesda, Md. The United States Government has certain rights in the invention.

BACKGROUND OF THE INVENTION

This invention relates to relatively short peptides about 6–45 residues in length, which are naturally available in minute amounts in the venom of the cone snails or analogs to the naturally available peptides, and which include one or more bromo-tryptophan residues.

The publications and other materials used herein to illuminate the background of the invention, and in particular, cases to provide additional details respecting the practice, are incorporated by reference, and for convenience are referenced in the following text by author and date and are listed alphabetically by author in the appended bibliography.

Mollusks of the genus Conus produce a highly toxic venom that enables them to carry out their unique predatory lifestyle. Prey are immobilized by the venom that is injected by means of a highly specialized venom apparatus, a disposable hollow tooth that functions both in the manner of a harpoon and a hypodermic needle.

Few interactions between organisms are more striking than those between a venomous animal and its envenomated victim. Venom may be used as a primary weapon to capture prey or as a defense mechanism. These venoms disrupt essential organ systems in the envenomated animal, and many of these venoms contain molecules directed to receptors and ion channels of neuromuscular systems.

The predatory cone snails (Conus) have developed a unique biological strategy. Their venom contains relatively small peptides that are targeted to various neuromuscular receptors and may be equivalent in their pharmacological diversity to the alkaloids of plants or secondary metabolites of microorganisms. Many of these peptides are among the smallest nucleic acid-encoded translation products having defined conformations, and as such, they are somewhat unusual. Peptides in this size range normally equilibrate among many conformations. Proteins having a fixed conformation are generally much larger.

The cone snails that produce these toxic peptides, which are generally referred to as conotoxins or conotoxin peptides, are a large genus of venomous gastropods comprising approximately 500 species. All cone snail species are predators that inject venom to capture prey, and the spectrum of animals that the genus as a whole can envenomate is broad. A wide variety of hunting strategies are used, however, every Conus species uses fundamentally the same basic pattern of envenomation.

Several peptides isolated from Conus venoms have been characterized. These include the α-, μ- and ω-conotoxins which target nicotinic acetylcholine receptors, muscle sodium channels, and neuronal calcium channels, respectively (Olivera et al., 1985). Conopressins, which are vasopressin analogs, have also been identified (Cruz et al. 1987). In addition, peptides named conantokins have been isolated from *Conus geographus* and *Conus tulipa* (Mena et al., 1990; Haack et al., 1990). These peptides have unusual age-dependent physiological effects: they induce a sleep-like state in mice younger than two weeks and hyperactive behavior in mice older than 3 weeks (Haack et al., 1990). Recently, peptides named contryphans containing D-tryptophan residues have been isolated from *Conus radiatus* (U.S. Ser. No. 60/).

The N-methyl-D-aspartate (NMDA) receptor is a postsynaptic ionotropic receptor which is responsive to the excitatory amino acids glutamate and glycine and the synthetic compound NMDA, among others. The NMDA receptor controls the flow of both divalent ($Ca^{2+}$) and monovalent ($K^+$, $Na^+$) ions into the postsynaptic neural cell through a receptor associated channel (Foster and Fagg, 1987; Mayer and Miller, 1990).

The NMDA receptor has been implicated during development in specifying neuronal architecture and synaptic connectivity, and may be involved in experience dependent synaptic modifications. In addition, NMDA receptors are also thought to be involved in long term potentiation, Central Nervous System (CNS) plasticity, cognitive processes, memory acquisition, retention and learning. The NMDA receptor has also drawn particular interest since it appears to be involved in a broad spectrum of CNS disorders. For example, during brain ischemia caused by stroke or traumatic injury, excessive amounts of the excitatory amino acid glutamate are released from damaged or oxygen deprived neurons. This excess glutamate binds to the NMDA receptor which opens the ligand-gated ion channel thereby allowing $Ca^{++}$ influx producing a high level of intracellular $Ca^{++}$ which activates biochemical cascades resulting in protein, DNA and membrane degradation leading to cell death. This phenomenon, known as excitotoxicity, is also thought to be responsible for the neurological damage associated with other disorders ranging from hypoglycemia and cardiac arrest to epilepsy. In addition, there are reports indicating similar involvement in the chronic neurodegeneration of Huntington's, Parkinson's and Alzheimer's diseases. Activation of the NMDA receptor has been shown to be responsible for post-stroke convulsions, and, in certain models of epilepsy, activation of the NMDA receptor has been shown to be necessary for the generation of seizures.

In addition to the effect of glutamate on the NMDA channel, it is also regulated by glycine. This amino acid increases NMDA-evoked currents in various tissues [Johnson and Ascher, 1987; Kleckner and Dingledine, 1988] by increasing the opening frequency of the NMDA channel [Johnson and Ascher, 1987]. Thus, NMDA-induced calcium influx and intracellular accumulation may therefor also be stimulated by glycine [Reynolds et al., 1987; Wroblewski et al., 1989], which interacts with its own distinct site [Williams et al., 1991].

Neuropsychiatric involvement of NMDA receptor has also been recognized. Blockage of the NMDA receptor $Ca^{2+}$ channel by the animal anesthetic PCP (phencyclidine) produces a psychotic state in humans similar to schizophrenia (Johnson and Jones, 1990). NMDA receptors have also been implicated in certain types of spatial learning (Bliss et al., 1993). Interestingly, both the spatial and temporal distribution of NMDA receptors in mammalian nervous systems have been found to vary. Thus, cells may produce NMDA receptors at different times in their life cycles and not all neural cells may utilize the NMDA receptor.

Specifically, it has been shown that neurotransmission mediated through the NMDA receptor complex is associated with seizures [Bowyer, 1982; McNamara et al., 1988], ischemic neuronal injury [Simon et al., 1984; Park et al., 1988] and other phenomena including synaptogenesis [Cline et al., 1987], spatial learning [Morris et al., 1986] and long-term potentiation [Collinridge et al., 1983; Harris et al., 1984; Morris et al., 1986]. Regulation of these neuronal mechanisms by NMDA-mediated processes may involve activation of a receptor-gated calcium ion channel [Nowak et al., 1984; Mayer et al., 1987; Ascher and Nowak, 1988].

Epilepsy is a recurrent paroxysmal disorder of cerebral function characterized by sudden brief attacks of altered consciousness, motor activity, sensory phenomena or inappropriate behavior caused by abnormal excessive discharge of cerebral neurons. Convulsive seizures, the most common form of attacks, begin with loss of consciousness and motor control, and tonic or clonic jerking of all extremities but any recurrent seizure pattern may be termed epilepsy. The term primary or idiopathic epilepsy denotes those cases where no cause for the seizures can be identified. Secondary or symptomatic epilepsy designates the disorder when it is associated with such factors as trauma, neoplasm, infection, developmental abnormalities, cerebrovascular disease, or various metabolic conditions. Epileptic seizures are classified as partial seizures (focal, local seizures) or generalized seizures (convulsive or nonconvulsive). Classes of partial seizures include simple partial seizures, complex partial seizures and partial seizures secondarily generalized. Classes of generalized seizures include absence seizures, atypical absence seizures, myoclonic seizures, clonic seizures, tonic seizures, tonic-clonic seizures (grand mal) and atonic seizures. Therapeutics having anticonvulsant properties are used in the treatment of seizures. Most therapeutics used to abolish or attenuate seizures demonstrate act at least through effects that reduce the spread of excitation from seizure foci and prevent detonation and disruption of function of normal aggregates of neurons. Anticonvulsants which have been utilized include phenytoin, phenobarbital, primidone, carbamazepine, ethosuximide, clonazepam and valproate. For further details of seizures and their therapy (see Rall & Schleifer (1985) and *The Merck Manual* (1992)).

The development of drugs acting at the NMDA receptor is described in U.S. Pat. Nos. 4,904,681; 5,061,721 and 5,086,072 and in PCT application publication numbers WO 94/07914 and WO 96/11698. It is desired to identify additional compounds which target the NMDA receptor. It is further desired to identify compounds which are useful as anticonvulsant or neuroprotective agents.

SUMMARY OF THE INVENTION

The present invention is directed to conopeptides having 6–45 amino acids, including one or more bromo-tryptophan residues. More specifically, the present invention is directed to conopeptides having the general formula: R-(Cys)$_n$-R$^1$-B-R$^2$-Cys-R$^3$, wherein R is a peptide chain of 0–24 amino acids, R$^1$ is a peptide of 0 to 31 amino acids, R$^2$ is a peptide chain of 0–29 peptides, R$^3$ is a peptide chanin of 0 to 26 amino acids, B is 6-bromo-tryptophan, n is 0 or 1 and the total length of the conopeptide is from about 6 to about 45 amino acids. The invention also includes pharmaceutically acceptable salts of the conopeptides. These bromo-tryptophan containing conopeptides are useful as antihelminthic agents, sleep-inducing agents, adjuncts to anesthesia, anticonvulsant or neuroprotective agents.

DETAILED DESCRIPTION OF THE PREFERRED EMBODIMENT

The present invention is directed to contryphan peptides having 6–45 amino acids, including one or more bromo-tryptophan residues. More specifically, the present invention is directed to conopeptides having the general formula: R-(Cys)$_n$-R$^1$-B-R$^2$-Cys-R$^3$, wherein R is a peptide chain of 0–24 amino acids, R$^1$ is a peptide chain of 0 to 31 amino acids, R$^2$ is a peptide chain of 0–29 amino acids, R$^3$ is a peptide chain of 0 to 26 amino acids, B is 6-bromo-tryptophan, n is 0 or 1 and the total length of the conopeptide is from about 6 to about 45 amino acids. The invention also includes pharmaceutically acceptable salts of the conopeptides. As used herein, the term "amino acid" means an α-amino acid. Included within this term are natural amino acids, including unusual amino acids such as γ-carboxyglutamate (Gla) and hydroxyproline (Hyp), D-amino acids such as D-tryptophan, as well as modified and non-natural amino acids, such as those described in, for example, Roberts et al. (1983).

Examples of conopeptides of the present invention include the followingcompounds.

Gly-Cys-Xaa$_1$-Xaa$_2$-Glu-Pro-Xaa$_3$-Cys, wherein Xaa$_1$ is Hyp or Pro, Xaa$_2$ is D-Trp and Xaa$_3$ is L-6-bromo-tryptophan (SEQ ID NO:1). Xaa$_1$ is preferably Hyp and the C-terminus preferably contains an amide. A peptide contains a disulfide bridge.

Xaa$_1$-Cys-Gly-Gln-Ala-Xaa$_2$-Cys, wherein Xaa$_1$ is Gla or Glu and Xaa$_2$ is L-6-bromo-tryptophan (SEQ ID NO:2). Xaa$_1$ is preferably Gla and the C-terminus preferably contains an amide. The peptide contains a disulfide bridge.

Xaa$_1$-Ala-Thr-Ile-Asp-Xaa$_2$-Cys-Xaa$_2$-Xaa$_2$-Thr-Cys-Asn-Val-Thr-Phe-Lys-Thr-Cys-Cys-Gly-Xaa$_3$-Xaa$_3$-Gly-Asp-Trp-Gln-Cys-Val-Xaa$_2$-Ala-Cys-Pro-Val, wherein Xaa$_1$ is L-6-bromo-tryptophan, Xaa$_2$ is Gla or Glu and Xaa$_3$ is Hyp or Pro (SEQ ID NO:3). Xaa$_2$ is preferably Gla, Xaa$_3$ is preferably Hyp and the C-terminus preferably contains a hydroxyl. The peptide contains three disulfide bridges.

Xaa$_1$-Ala-Thr-Ile-Asp-Xaa$_2$-Cys-Xaa$_2$-Xaa$_2$-Thr-Cys, wherein Xaa$_1$ is L-6-bromo-tryptophan and Xaa$_2$ is Gla or Glu (SEQ ID NO:4). Xaa$_2$ is preferably Gla and the C-terminus preferably contains a hydroxyl.

Xaa$_1$-Ala-Thr-Ile-Asp-Xaa$_2$-Cys-Xaa$_2$-Xaa$_2$-Thr-Cys-Asn-Val-Thr-Phe-Lys-Thr-Cys, wherein Xaa$_1$ is L-6-bromo-tryptophan and Xaa$_2$ is Gla or Glu (SEQ ID NO:5). Xaa$_2$ is preferably Gla and the C-terminus preferably contains a hydroxyl.

Xaa$_1$-Ala-Thr-Ile-Asp-Xaa$_2$-Cys-Xaa$_2$-Xaa$_2$-Thr-Cys-Asn-Val-Thr-Phe-Lys-Thr-Cys-Cys-Gly-, wherein Xaa$_1$ is L-6-bromo-tryptophan and Xaa$_2$ is Gla or Glu (SEQ ID NO:6). Xaa$_2$ is preferably Gla and the C-terminus preferably contains a hydroxyl.

Xaa$_1$-Ala-Thr-Ile-Asp-Xaa$_2$-Cys-Xaa$_2$-Xaa$_2$-Thr-Cys-Asn-Val-Thr-Phe-Lys-Thr-Cys-Cys-Gly-Xaa$_3$-Xaa$_3$-Gly, wherein Xaa$_1$ is L-6-bromo-tryptophan, Xaa$_2$ is Gla or Glu and Xaa$_3$ is Hyp or Pro (SEQ ID NO:7). Xaa$_2$ is preferably Gla, Xaa$_3$ is preferably Hyp and the C-terminus preferably contains a hydroxyl.

Xaa$_1$-Ala-Thr-Ile-Asp-Xaa$_2$-Cys-Xaa$_2$-Xaa$_2$-Thr-Cys-Asn-Val-Thr-Phe-Lys-Thr-Cys-Cys-Gly-Xaa$_3$-Xaa$_3$-Gly-Asp-Trp-Gln-Cys, wherein Xaa$_1$ is L-6-bromo-tryptophan, Xaa$_2$ is Gla or Glu and Xaa$_3$ is Hyp or Pro (SEQ ID NO:8). Xaa$_2$ is preferably Gla, Xaa$_3$ is preferably Hyp and the C-terminus preferably contains a hydroxyl.

Xaa$_1$-Ala-Thr-Ile-Asp-Xaa$_2$-Cys-Xaa$_2$-Xaa$_2$-Thr-Cys-Asn-Val-Thr-Phe-Lys-Thr-Cys-Cys-Gly-Xaa$_3$-Xaa$_3$-Gly-Asp-Trp-Gln-Cys-Val-Xaa$_2$-Ala, wherein Xaa$_1$ is L-6-bromo-tryptophan, Xaa$_2$ is Gla or Glu and Xaa$_3$ is Hyp or Pro (SEQ ID NO:9). Xaa$_2$ is preferably Gla, Xaa$_3$ is preferably Hyp and the C-terminus preferably contains a hydroxyl.

Gly-Cys-Thr-Arg-Thr-Cys-Gly-Gly-Xaa$_1$-Lys-Cys-Thr-Gly-Thr-Cys-Thr-Cys-Thr-Asn-Ser-Ser-Lys-Cys-Gly-Cys-

Arg-Tyr-Asn-Val-His-Pro-Ser-Gly-Xaa$_2$-Gly-Cys-Gly-Cys-Ala-Cys-Ser, wherein Xaa$_1$ is Hyp or Pro and Xaa$_2$ is 6-bromo-L-tryptophan (SEQ ID NO:10). Xaa$_1$ is preferably Hyp.

Thr-Arg-Thr-Cys-Gly-Gly-Xaa$_1$-Lys-Cys-Thr-Gly-Thr-Cys-Thr-Cys-Thr-Asn-Ser-Ser-Lys-Cys-Gly-Cys-Arg-Tyr-Asn-Val-His-Pro-Ser-Gly-Xaa$_2$-Gly-Cys-Gly-Cys-Ala-Cys-Ser, wherein Xaa$_1$ is Hyp or Pro and Xaa$_2$ is 6-bromo-L-tryptophan (SEQ ID NO:11). Xaa$_1$ is preferably Hyp.

Gly-Gly-Xaa$_1$-Lys-Cys-Thr-Gly-Thr-Cys-Thr-Cys-Thr-Asn-Ser-Ser-Lys-Cys-Gly-Cys-Arg-Tyr-Asn-Val-His-Pro-Ser-Gly-Xaa$_2$-Gly-Cys-Gly-Cys-Ala-Cys-Ser, wherein Xaa$_1$ is Hyp or Pro and Xaa$_2$ is 6-bromo-L-tryptophan (SEQ ID NO:12). Xaa$_1$ is preferably Hyp.

The conopeptides of the present invention have a bromo-tryptophan residue. This is the first report of bromo-tryptophan being formed through post-translational modification in the Conus snails. Like most peptides found in Conus venoms, the conopeptides of the present invention contain one or more disulfide bonds when the conopeptide contains multiple cysteine residues.

These bromo-tryptophan containing conopeptides invention are useful as antihelminthic agents, anti-vomiting agents, sleep-inducing agents, adjuncts to anesthesia, anti-convulsant or neuroprotective agents. Certain of the conopeptides have anticonvulsant activity in Fringes audiogenic seizure susceptible mice and in syndrome-specific seizure animal models. Such conopeptides are useful as anticonvulsant agents, as neuroprotective agents, for managing pain and for treating neurodegenerative disorders, especially those resulting from an overstimulation of excitatory amino acid receptors. Thus, certain conopeptides of the present invention are useful for the treatment and alleviation of epilepsy and as a general anticonvulsant agent. Certain conopeptides are also useful to reduce neurotoxic injury associated with conditions of hypoxia, anoxia or ischemia which typically follows stroke, cerebrovascular accident, brain or spinal chord trauma, myocardial infarct, physical trauma, drownings, suffocation, perinatal asphyxia, or hypoglycemic events. Certain conopeptides are further useful for the treatment of Alzheimer's disease, senile dementia, Amyotrophic Lateral Sclerosis, Parkinson's disease, Huntington's disease, Down's Syndrome, Korsakoff's disease, schizophrenia, AIDS dementia, multi-infarct dementia, mood disorders, depression, chemical toxicity and neuronal damage associated with uncontrolled seizures. The conopeptides are further useful in controlling pain and are effective in the treatment of migraine. They can be used prophylactically or to relieve the symptoms associated with a migraine episode.

These peptides are sufficiently small to be chemically synthesized. General chemical syntheses for preparing the foregoing conopeptides peptides are described hereinafter, along with specific chemical synthesis of conopeptides and indications of biological activities of these synthetic products. Various ones of these conopeptides can also be obtained by isolation and purification from specific Conus species using the technique described in U.S. Pat. No. 4,447,356 (Olivera et al., 1984), the disclosure of which is incorporated herein by reference.

Although the conopeptides of the present invention can be obtained by purification from cone snails, because the amounts of conopeptides obtainable from individual snails are very small, the desired substantially pure conopeptides are best practically obtained in commercially valuable amounts by chemical synthesis using solid-phase strategy. For example, the yield from a single cone snail may be about 10 micrograms or less of conopeptide. By "substantially pure" is meant that the peptide is present in the substantial absence of other biological molecules of the same type; it is preferably present in an amount of at least about 85% purity and preferably at least about 95% purity. Chemical synthesis of biologically active conopeptides depends of course upon correct determination of the amino acid sequence.

The conopeptides can also be produced by recombinant DNA techniques well known in the art. Such techniques are described by Sambrook et al. (1979). The peptides produced in this manner are isolated, reduced if necessary, and oxidized to form the correct disulfide bonds.

One method of forming disulfide bonds in the conopeptides of the present invention is the air oxidation of the linear peptides for prolonged periods under cold room temperatures or at room temperature. This procedure results in the creation of a substantial amount of the bioactive, disulfide-linked peptides. The oxidized peptides are fractionated using reverse-phase high performance liquid chromatography (HPLC) or the like, to separate peptides having different linked configurations. Thereafter, either by comparing these fractions with the elution of the native material or by using a simple assay, the particular fraction having the correct linkage for maximum biological potency is easily determined. It is also found that the linear peptide, or the oxidized product having more than one fraction, can sometimes be used for in vivo administration because the cross-linking and/or rearrangement which occurs in vivo has been found to create the biologically potent conopeptide molecule. However, because of the dilution resulting from the presence of other fractions of less biopotency, a somewhat higher dosage may be required.

The peptides are synthesized by a suitable method, such as by exclusively solid-phase techniques, by partial solid-phase techniques, by fragment condensation or by classical solution couplings.

In conventional solution phase peptide synthesis, the peptide chain can be prepared by a series of coupling reactions in which constituent amino acids are added to the growing peptide chain in the desired sequence. Use of various coupling reagents, e.g., dicyclohexylcarbodiimide or diisopropylcarbonyldimidazole, various active esters, e.g., esters of N-hydroxyphthalimide or N-hydroxy-succinimide, and the various cleavage reagents, to carry out reaction in solution, with subsequent isolation and purification of intermediates, is well known classical peptide methodology. Classical solution synthesis is described in detail in the treatise, "Methoden der Organischen Chemie (Houben-Weyl): Synthese von Peptiden," (1974). Techniques of exclusively solid-phase synthesis are set forth in the textbook, "Solid-Phase Peptide Synthesis," (Stewart and Young, 1969), and are exemplified by the disclosure of U.S. Pat. No. 4,105,603 (Vale et al., 1978). The fragment condensation method of synthesis is exemplified in U.S. Pat. No. 3,972,859 (1976). Other available syntheses are exemplified by U.S. Pat. Nos. 3,842,067 (1974) and 3,862,925 (1975). The synthesis of peptides containing γ-carboxyglutamic acid residues is exemplified by Rivier et al. (1987), Nishiuchi et al. (1993) and Zhou et al. (1996).

Common to such chemical syntheses is the protection of the labile side chain groups of the various amino acid moieties with suitable protecting groups which will prevent a chemical reaction from occurring at that site until the group is ultimately removed. Usually also common is the protection of an α-amino group on an amino acid or a fragment while that entity reacts at the carboxyl group, followed by the selective removal of the α-amino protecting group to allow subsequent reaction to take place at that location. Accordingly, it is common that, as a step in such a synthesis, an intermediate compound is produced which includes each of the amino acid residues located in its desired sequence in the peptide chain with appropriate side-chain protecting groups linked to various ones of the residues having labile side chains.

As far as the selection of a side chain amino protecting group is concerned, generally one is chosen which is not removed during deprotection of the α-amino groups during the synthesis. However, for some amino acids, e.g., His, protection is not generally necessary. In selecting a particular side chain protecting group to be used in the synthesis of the peptides, the following general rules are followed: (a) the protecting group preferably retains its protecting properties and is not split off under coupling conditions, (b) the protecting group should be stable under the reaction conditions selected for removing the α-amino protecting group at each step of the synthesis, and (c) the side chain protecting group must be removable, upon the completion of the synthesis containing the desired amino acid sequence, under reaction conditions that will not undesirably alter the peptide chain.

It should be possible to prepare many, or even all, of these peptides using recombinant DNA technology. However, when peptides are not so prepared, they are preferably prepared using the Merrifield solid-phase synthesis, although other equivalent chemical syntheses known in the art can also be used as previously mentioned. Solid-phase synthesis is commenced from the C-terminus of the peptide by coupling a protected α-amino acid to a suitable resin. Such a starting material can be prepared by attaching an α-amino-protected amino acid by an ester linkage to a chloromethylated resin or a hydroxymethyl resin, or by an amide bond to a benzhydrylamine (BHA) resin or param-ethylbenzhydrylamine (MBHA) resin. Preparation of the hydroxymethyl resin is described by Bodansky et al. (1966). Chloromethylated resins are commercially available from Bio Rad Laboratories (Richmond, Calif.) and from Lab. Systems, Inc. The preparation of such a resin is described by Stewart et al. (1969). BHA and MBHA resin supports are commercially available, and are generally used when the desired polypeptide being synthesized has an unsubstituted amide at the C-terminus. Thus, solid resin supports may be any of those known in the art, such as one having the formulae —O—CH$_2$-resin support, —NH BHA resin support, or —NH—MBHA resin support. When the unsubstituted amide is desired, use of a BHA or MBHA resin is preferred, because cleavage directly gives the amide. In case the N-methyl amide is desired, it can be generated from an N-methyl BHA resin. Should other substituted amides be desired, the teaching of U.S. Pat. No. 4,569,967 (Kornreich et al., 1986) can be used, or should still other groups than the free acid be desired at the C-terminus, it may be preferable to synthesize the peptide using classical methods as set forth in the Houben-Weyl text (1974).

The C-terminal amino acid, protected by Boc or Fmoc and by a side-chain protecting group, if appropriate, can be first coupled to a chloromethylated resin according to the procedure set forth in K. Horiki et al. (1978), using KF in DMF at about 60° C. for 24 hours with stirring, when a peptide having free acid at the C-terminus is to be synthesized. Following the coupling of the BOC-protected amino acid to the resin support, the α-amino protecting group is removed, as by using trifluoroacetic acid (TFA) in methylene chloride or TFA alone. The deprotection is carried out at a temperature between about 0° C. and room temperature. Other standard cleaving reagents, such as HCl in dioxane, and conditions for removal of specific α-amino protecting groups may be used as described in Schroder & Lubke (1965).

After removal of the α-amino-protecting group, the remaining α-amino- and side chain-protected amino acids are coupled step-wise in the desired order to obtain the intermediate compound defined hereinbefore, or as an alternative to adding each amino acid separately in the synthesis, some of them may be coupled to one another prior to addition to the solid phase reactor. Selection of an appropriate coupling reagent is within the skill of the art. Particularly suitable as a coupling reagent is N,N'-dicyclohexylcarbodiimide (DCC, DIC, HBTU, HATU, TBTU in the presence of HoBt or HoAt).

The activating reagents used in the solid phase synthesis of the peptides are well known in the peptide art. Examples of suitable activating reagents are carbodiimides, such as N,N'-diisopropylcarbodiimide and N-ethyl-N'-(3-dimethylaminopropyl)carbodiimide. Other activating reagents and their use in peptide coupling are described by Schroder & Lubke (1965) and Kapoor (1970).

Each protected amino acid or amino acid sequence is introduced into the solid-phase reactor in about a twofold or more excess, and the coupling may be carried out in a medium of dimethylformamide (DMF):CH$_2$Cl$_2$ (1:1) or in DMF or CH$_2$Cl$_2$ alone. In cases where intermediate coupling occurs, the coupling procedure is repeated before removal of the α-amino protecting group prior to the coupling of the next amino acid. The success of the coupling reaction at each stage of the synthesis, if performed manually, is preferably monitored by the ninhydrin reaction, as described by Kaiser et al. (1970). Coupling reactions can be performed automatically, as on a Beckman 990 automatic synthesizer, using a program such as that reported in Rivier et al. (1978).

After the desired amino acid sequence has been completed, the intermediate peptide can be removed from the resin support by treatment with a reagent, such as liquid hydrogen fluoride or TFA (if using Fmoc chemistry), which not only cleaves the peptide from the resin but also cleaves all remaining side chain protecting groups and also the α-amino protecting group at the N-terminus if it was not previously removed to obtain the peptide in the form of the free acid. If Met is present in the sequence, the Boc protecting group is preferably first removed using trifluoroacetic acid (TFA)/ethanedithiol prior to cleaving the peptide from the resin with HF to eliminate potential S-alkylation. When using hydrogen fluoride or TFA for cleaving, one or more scavengers such as anisole, cresol, dimethyl sulfide and methylethyl sulfide are included in the reaction vessel.

The synthesis of conopeptides containing a bromo-tryptophan residue is accomplished in a similar manner using racemic bromo-tryptophan as described herein. The resulting bromo-D-tryptophan and bromo-L-tryptophan conopeptides are then separated using conventional techniques or as described herein.

Cyclization of the linear peptide is preferably affected, as opposed to cyclizing the peptide while a part of the peptido-resin, to create bonds between Cys residues. To effect such a disulfide cyclizing linkage, fully protected peptide can be cleaved from a hydroxymethylated resin or a chloromethylated resin support by ammonolysis, as is well known in the art, to yield the fully protected amide intermediate, which is thereafter suitably cyclized and deprotected. Alternatively, deprotection, as well as cleavage of the peptide from the above resins or a benzhydrylamine (BHA) resin or a methylbenzhydrylamine (MBHA), can take place at 0° C. with hydrofluoric acid (HF) or TFA, followed by oxidation as described above.

Certain conopeptides of the present invention are antagonists of the NMDA receptor sites and are useful as anticonvulsant agents, as neuroprotective agents, for managing pain and for treating neurodegenerative disorders, especially those resulting from an overstimulation of excitatory amino acid receptors. Thus, such conopeptides of the present invention are useful for the treatment and alleviation of epilepsy and as a general anticonvulsant agent. The use of conopeptides in these conditions includes the administration of a conopeptide in a therapeutically effective amount to patients in need of treatment. The conopeptides can be used to treat the seizures to reduce their effects and to prevent seizures.

Certain conopeptides are also useful to reduce neurotoxic injury associated with conditions of hypoxia, anoxia or ischemia which typically follows stroke, cerebrovascular accident, brain or spinal chord trauma, myocardial infarct, physical trauma, drownings, suffocation, perinatal asphyxia, or hypoglycemic events. To reduce neurotoxic injury, the conopeptides should be administered to the patient within 24 hours of the onset of the hypoxic, anoxic or ischemic condition in order for the contryphans to effectively minimize the CNS damage which the patient will experience.

Certain conopeptides are further useful for the treatment of Alzheimer's disease, senile dementia, Amyotrophic Lateral Sclerosis, Parkinson's disease, Huntington's disease, Down's Syndrome, Korsakoff's disease, schizophrenia, AIDS dementia, multi-infarct dementia, and neuronal damage associated with uncontrolled seizures. The administration of such conopeptides to a patient experiencing such conditions will serve to either prevent the patient form experiencing further neurodegeneration or it will decrease the rate at which neurodegeneration occurs. Certain conopeptides are further useful in controlling pain and are effective in the treatment of migraine. They can be used prophylactically or to relieve the symptoms associated with a migraine episode.

The anticonvulsant effects of conopeptides are demonstrated in animal models. In rodents, conopeptides are effective against supramaximal tonic extension seizures produced by maximal electroshock and threshold seizures induced by s.c. pentylenetetrazol or picrotoxin. Conopeptides are also effective against focal seizures induced by aluminum hydroxide injection into the pre- and post-central gyri of rhesus monkeys. Conopeptides when administered to patients with refractory complex partial seizures may markedly reduced seizure frequency and severity. Moreover, the clinical utility of conopeptides as a therapeutic agent for epilepsy may include generalized tonic-clonic and complex partial seizures.

Studies in laboratory animal models demonstrate the neuroprotectant properties of conopeptides. Conopeptides protect against hypoxic damage to the hippocampal slice in vitro. In neonate rats, conopeptides reduce the size of cortical infarcts and amount of hippocampal necrosis following bilateral carotid ligation and hypoxia. The conopeptides may also be effective anti-pain agents.

For newly diagnosed patients with a seizure disorder and patients with seizure disorders for whom changes in drugs are being made, a relatively low dosage of drug is started and increased over a week or so to a standard therapeutic dosage. After about a week at such dosage, blood levels are obtained to determine the patient's pharmacokinetic response and, if appropriate, whether the effective therapeutic level has been reached. If seizures continue, the daily dosage is increased by small increments as dosage rises above the usual. Once seizures are brought under control, the drug should be continued without interruption at least one seizure-free year. At that time, discontinuation of the drug should be considered, since about 50% of such patients will remain seizure free without drugs. Patients whose attacks initially were difficult to control, those who failed a therapy-free trial and those with important social reasons for avoiding seizures should be treated indefinitely.

Certain conopeptides of the present invention, such as those originally isolated from worm hunters including *Conus imperialis*, are useful as antihelminthic agents. These conopeptides are used to treat patients with parasitic worms in a conventional manner. Certian conopeptides of the present inventions, such as those which bind to the $5HT_3$ serotonin receptor, are useful as antivomiting agents.

Pharmaceutical compositions containing a compound of the present invention as the active ingredient can be prepared according to conventional pharmaceutical compounding techniques. See, for example, *Remington's Pharmaceutical Sciences*, 17th Ed. (1985, Mack Publishing Co., Easton, Pa.). Typically, an antagonistic amount or an antihelminthic amount of the active ingredient will be admixed with a pharmaceutically acceptable carrier. The carrier may take a wide variety of forms depending on the form of preparation desired for administration, e.g., intravenous, oral or parenteral. The compositions may further contain antioxidizing agents, stabilizing agents, preservatives and the like.

For oral administration, the compounds can be formulated into solid or liquid preparations such as capsules, pills, tablets, lozenges, melts, powders, suspensions or emulsions. In preparing the compositions in oral dosage form, any of the usual pharmaceutical media may be employed, such as, for example, water, glycols, oils, alcohols, flavoring agents, preservatives, coloring agents, suspending agents, and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. If desired, tablets may be sugar-coated or enteric-coated by standard techniques. The active agent can be encapsulated to make it stable to passage through the gastrointestinal tract while at the same time allowing for passage across the blood brain barrier. See for example, WO 96/11698.

For parenteral administration, the compound may dissolved in a pharmaceutical carrier and administered as either a solution of a suspension. Illustrative of suitable carriers are water, saline, dextrose solutions, fructose solutions, ethanol, or oils of animal, vegetative or synthetic origin. The carrier may also contain other ingredients, for example, preservatives, suspending agents, solubilizing agents, buffers and the like. When the compounds are being administered intrathecally, they may also be dissolved in cerebrospinal fluid.

The conopeptides are administered in an amount sufficient to antagonize the effects of excitatory amino acids or other agonists upon the NMDA receptor complex. The dosage range at which the conopeptides exhibit this antagonistic effect can vary widely depending upon the particular disease being treated, the severity of the patient's disease, the patient, the specific contryphan being administered, the route of administration and the presence of other underlying disease states within the patient. Typically the conopeptides exhibit their therapeutic effect at a dosage range from about 0.05 mg/kg to about 250 mg/kg, and preferably from about 0.1 mg/kg to about 100 mg/kg of the active ingredient. A suitable dose can be administered in multiple sub-doses per day. Typically, a dose or sub-dose may contain from about 0.1 mg to about 500 mg of the active ingredient per unit dosage form. A more preferred dosage will contain from about 0.5 mg to about 100 mg of active ingredient per unit dosage form. Dosages are generally initiated at lower levels and increased until desired effects are achieved. Similar dosages of conopeptides as antihelminthic agents are administered to patients with parasitic worms. Similar dosages of conopeptides as anti-vomiting agents are administered to patients in need of such agents, such as patients undergoing chemothrapy.

EXAMPLES

The present invention is described by reference to the following Examples, which are offered by way of illustration and are not intended to limit the invention in any manner. Standard techniques well known in the art or the techniques specifically described below were utilized. The following abbreviations are used in the examples: Boc: tert-butoxycarbonyl; Cys(Cam): S-carboxyamidomethylcysteine; Cys(Mob): S-p-mthoxybenzyl-L-cysteine; CZE: capillary zone electrophoresis; Chx: cyclohexyl; DCM: chloromethane; DIC: diisopropylcarbodiimide; DIEA: diisopropylethylamine; Fmoc: 9-fluorenylmethoxycarbonyl; Gln(Xnt): N-g-xanthyl-L-glutamine; HOBt: 1-hydroxy-benzotriazole; HPLC: high-performance liquid chromatography; LSI: liquid secondary ionization; MALD: matrix assisted laser absorption; MBHA: 4 methylbenzyhydrylamine; Mob: 5-p-methoxyphenol; MS: mass spectrometry; NMP: N-methylpyrrolidone; PTH: phenylthiohydantoid derivative; Pca: pyroglutamic acid; TBTU: O-(benzo-triazole-1-yl)-NNN$^7$N$^7$-tetramethyluronium tetrafluoroborate; TCEP: tris(2-carboxyethyl)phosphine; TEAP: triethylamine phophate; TFA: trifluoroacetic acid; and, TMAC: tetramethylammonium chloride.

Example 1

Methods Relating to Bromocontryphan

Reagents: Boc-Cys(Mob)—OH, Boc-Glu(Chx)—OH, Boc-Trp—OH, Boc-D-Trp—OH, Boc-Hypro—OH, and Boc-Gly—OH (Bachem, Torrance, Calif.); D,L-6-bromotryptophan (Biosynth AG, Staad, Switzerland).

Purification of the Peptides. Crude venom was extracted from venom ducts (Cruz et al., 1976), and the components were purified as previously described (Jimenez et al., 1996). The crude extract from venom ducts was applied into a $C_{18}$ semi-preparative column (10×250 mm) and eluted with a linear gradient of acetonitrile in 0.085% TFA at 5 mL/min. Further purification of bioactive peaks was done on a $C_{18}$ analytical column (4.6×250 mm) eluted with a gradient of acetonitrile in 0.085% TFA at 1 mL/min. The effluents were monitored at 220 nm. Peaks were collected, and aliquots were assayed for activity.

Bioassays. Biological activity was assayed by intracranial injection in mice (9 to 21 days old for "stiff-tail" activity; 9, 17 and 22 days old for sleeper activity). Aliquots of peptide samples were lyophilized and dissolved in normal saline solution and then injected into mice using a 0.3 mL syringe with a 29-gauge needle. Each control mouse was injected with an equal volume of normal saline solution containing dissolved residue of lyophilized column buffer blanks. After injection, the mice were placed in cages for observation.

Peptide Sequencing. The purified peptides were reduced and alkylated as described by Shon et al. (1994) prior to sequencing by automated Edman degradation on an Applied Biosystems 477A Protein Sequencer with a 120A Analyzer (DNA/Peptide Facility, University of Utah).

Mass Spectrometry. Matrix assisted laser desorption mass spectra were measured using a Bruker REFLEX (Bruker Instruments Inc., Bremen, Germany) time-of-flighyt mass spectrometer fillted with a gridless reflection and $N_2$ laster and a 200 Mhz digitizer. The sample (in 0.1% aqueous TFA) was applied with α-cyano-4-hydroxycinnamic acid and rinsed with water. Analysis was done with an accelerating voltage of +31 kV and a maximum reflector voltage of +30 kV. Under these conditions, the mass accuracy obtained was typically better than 200 ppm in the reflectron mode.

Liquid secondary ionization and matrix-assisted laser desorption mass spectra were measured using a Jeol HX110 (Tokyo, Japan) double-focusing mass spectrometer operated at 10 kV accelerating voltage and a nominal resolution of 3,000. The intact bromotryptophan sample was analyzed with MALD-MS and an electrie field scan. The spectra were calibrated using peptide calibrants over a narrow mass range. The HPLC-purified product of carboxypeptidase hydrolysis was concentrated from 100 to 10 μL, mixed in a glycerol 3-nitrobenzyl alcohol matrix (1:1), and analyzed with LSI-MS using a magnetic field scan. The LSI-MS spectra were calibrated using $[Cs(CsI)_n]^+$ cluster ions; the mass accuracy was typically better than 50 ppm.

Carboxypeptidase Y Hydrolysis. The reduced TCEP and alkylated (iodoacetamide) synthetic bromocontryplan (and analogs) were incubated with carboxypeptidase Y (1:5 enzyme: substrate) in 200 μL of 50 mM sodium acetate buffer (pH 5.5) at 22° C. for up to seven days. The reaction was monitored with HPLC and MALD-MS after one-, two-, four- and seven-day time intervals.

Peptide Synthesis and Purification. Bromocontryphan analogs (I) $GCX_1X_2EPX_3C$—$NH_2$, where $X_1$ is Hyp, $X_2$ is D-Trp and $X_3$ is 6-bromo-D,L-Trp (SEQ ID NO:13) and (II) $GCX_1WEPX_3C$—$NH_2$, where $X_1$ is Hyp and $X_3$ is 6-bromo-D,L-Trp (SEQ ID NO:14) were synthesized using Boc-6-bromo-D,L-tryptophan generated from 6-bromo-D,L-tryptophan using standard procedures. The two diastereomers of peptide (I) were separated, (Ia) $GCX_1X_2EPX_5C$—$NH_2$, $X_1$ is Hyp, $X_2$ is D-Trp and $X_5$ is 6-bromo-L-Trp (SEQ ID NO:1) and (Ib) $GCX_1X_2EPX_6C$—$NH_2$, $X_1$ is Hyp, $X_2$ is D-Trp and $X_6$ is 6-bromo-D-Trp (SEQ ID NO:15), by HPLC, whereas the two diastereomers of peptide (II) were not separated and used as an approximate 50:50% mixture for assays The synthesis of peptide mixtures (I) and (II) was performed on MBHA resin (1.0 g, substitution 0.5 mequiv/g) using Boc-Cys(Mob), (D,L)-Fmoc-6-Br-Trp—OH, Boc-Hypro—OH, and Boc-Glu(Chx)—OH for the first four residues. The resin was split, and the fifth residue was added using Boc-Trp—OH or Boc-D-Trp—OH. Boc-Hypro—OH, Boc-Cys(Mob)—OH, and Boc-Gly—OH were used to add the last three residue. The coupling steps were carried out in DCM with DIC as condensing agent. The Fmoc group of the bromotryptophan residue was removed with 20% NMP in piperidine for 2×10 minutes. The efficiency of each coupling reaction was checked by the Kaiser ninhydrin test. After removal of the final Boc protecting group, the peptide resin was washed with appropriate solvents and dried. The peptide resins (750 mg for the L-Trp-containing analog) were treated with 10 mL of HF in the presence of 1.0 mL of anisole at 0° C. for 1.5 hours. After the evaporation of HF, a first extraction was carried out with ether (3×25 mL) and a second extraction with 0.1% aqueous TFA and 60% acetonitrile (3×25 mL). Both aqueous peptide solutions gave a strong Ellman's positive test for free thiol groups. The acetonitrile-containing aqueous extracts of the crude peptide were diluted to 1,400 mL with 0.125M ammonium acetate (pH 6.9) and 200 mL of acetonitrile was added as the solution turned clear. Thr reaction mixture was stirred slowly in a 2 L beaker for 36 hours until the Ellman test turned to negative. The pH of the solution was adjusted to 2.2 by adding TFA, and acetonitrile was removed by rotary evaporation.

The crude oxidized peptide solution (1,000 mL) was filtered and loaded onto a Waters PrepLC/SAystem 500A equipped with gradient controller, Waters model 450 variable wavelength detector, and Waters 1000 PrepPack cartridge chamber (65.5×320 mm) column, packed with Vydac $C_{18}$ 15–20 mm particles; wavelength, 220 nm; AUFS, 2.0; flow, 100 mL/min; gradient, 0–50% in 100 min; buffer A, 0.1%; buffer B, 60% acetonitrile in 0.1% aqueous TFA. The fractions (50–75 mL) were collected mnually and analyzed by HPLC. Fractions with acceptable purity as determined by CZE analysis were pooled and lyophilized. The major component was collected and lyophilized (D-Trp$^4$; hydrophilic component, 3.0 mg; purity based on CZE 99.95; hydrophobic component, 14.6 mg; purity based on CZE 92%; L-Trp$^4$; major component, 12.6 mg).

Comparison of Natural and Synthetic Peptides: The various bromocontryphan analogs were applied separately to a $C_{18}$ analytical column and eluted at a flow rate of 1 mL/min with a gradient of ACN in 0.085% TFA. Aliquots of natural and synthetic bromocontryphan were co-injected and eluted under the same HPLC conditions.

Identification and Sequencing of a cDNA Clone Encoding Bromocontryphan: Bromo-contryphan-encoding clones were selected from a size-fractionated cDNA library constructed using MRNA obtained from *Conus radiatus* venom duct as previously described (Colledge et al., 1992). The library was screened using a bromocontryphan-specific probe corresponding to the last six amino acids of the peptide (5' CCR CAC CAN GGY TCC CA 3'(SEQ ID NO:16), where R=A or G, N=A or C or G or T, and Y=C or T). The oligonucleotide was end-labeled with γ-$^{32}$P]ATP using T$_4$ polynucleotide kinase and hybridized to sets of duplicate nylon filters (Hybond-N, Amersham) to which colonies of the *Conus radiatus* cDNA library were bound. Hybridization was done for 48 hours at 48° C. in 3M TMAC, 0.1M sodium phosphate, pH 6.8, 1.0 mM EDTA, 5× Denhardt's solution, 0.6% SDS, and 100 mg/mL salmon sperm DNA. After being washed at 50° C. in 3M TMAC, 50 mM Tris pH 8.0, 0.2% SDS followed by a room temperature wash in 2× SSC, 0.1% SDS, positive colonies were identified by autoradiography.

A secondary screening by polymerase chain reaction was performed on 20 of 42 clones that hybridized to this probe. Putative bromotryptophan clones were amplified by PCR using the above probe as the first primer and a second primer corresponding to a portion of the plasmid vector upstream of the site into which the cDNA library was cloned (5' GTT GTG TGG AAT TGT GAG CGG A 3'; SEQ ID NO:17). The PCR reaction was carried out in a 10 μL sealed capillary using an Idaho Technology air thermocycler. Each reaction contained one colony, 5 pmol of each primer, and 0.5 unit of Taq polymerase (Boehringer Mannheim) in a buffer consisting of 50 mM Tris, pH 8.3, 250 μg/mL BSA, and 2 mM MgCl$_2$. Reaction conditions were as follows: three minutes of pre-denaturation at 94° C. followed by 45 cycles, through denaturation (94° C., 5s), annealing (50° C., pulse), and elongation (72° C., 15s) steps.

Clones identified in the secondary screen were prepared by DNA sequencing as previously described (Monje et al., 1993). The nucleic acid sequence was determined according to the standard protocol for Sequenase version 2.0 DNA sequencing kit using the non-biotinylated vector primer and [$^{35}$S]ATP.

Example 2

Purification and Characterization of Bromocontryphan

Purification and characterization of two D-amino acid-containing compounds, contryphan R and des [Gly$^1$] contryphan R, was previously described (Jimenez et al., 1996). A third fraction from *Conus radiatus* venom was discovered which elicited the same general biological activity as the two previous peptides, but which eluted later on an HPLC column. The basic biological assay used to follow the peptide during various purification steps was intracranial injection and scoring for the "stiff tail syndrome" previously described by Jimenez et al. (1996).

The amino acid sequence of the purified peptide was determined by standard methods. The results of the amino acid sequencing run revealed an octapeptide with the sequence GCX$_1$X$_2$EPXC, where X$_1$ is Hyp, X$_2$ is D-Trp and X is a blank cycle (SEQ ID NO:18). This sequence is the same sequence as contryphan R (previously reported by Jimenez et al., 1996), except that in position 7, no assignment could be made. Thus, the peptide was closely related to contryphan, and had similar activity when injected into mice. Since contryphan has an L-Trp at the homologous position, the possibility was considered that a modified Trp was present in position 7 of the new peptide.

MALD-time-of-flight MS analysis of the purified fraction of bromocontryphan indicated partially resolved species at m/z 1068.8, 1070.5, and a separate species at m/z 1092.9. The species m/z 1070.5 and 1092.9 were interpreted as corresponding with intact [M+H]$^+$ and [M+Na]$^+$ molecular ions. MALD-MS analysis with a magnetic sector instrument of the purified peptide was also carried out, and relatively intense species were observed at m/z 1090.2, 1092.2, 1106.2 and 1108.2. The results with the higher resolution of the magnetic sector instrument were interpreted as the major isotopomers of the [M+H]$^+$ and [M+Na]$^+$ species, which would indicate an intact molecular mass of 1067.2 Da. These results indicate that the missing residue has a mass of 264 Da for the free acid. The results are consistent with the missing residue in position 7 being bromotryptophan and the peptide being C-terminal amidated (the observed monoisotopic mass of m/z 1090.2 is consistent with the calculated monoisotopic [M+Na]$^+$ of 1090.25 Da). It is noted that both contryphan R and des[Gly$^1$]contryphan R are also C-terminally amidated. These data indicate that the sequence of the octapeptide is Gly-Cys-Xaa$_1$-Xaa$_2$-Glu-Pro-Xaa$_3$-Cys—NH$_2$, where where Xaa$_1$ is Hyp, Xaa$_2$ is D-Trp and Xaa$_3$ is a bromo-Trp (SEQ ID NO 1:).

Example 3

Chemical Synthesis of Bromocontryphan

However, the data in Example 2 do not reveal the location on tryptophan where the putative bromination takes place. Both the 5- and 6-bromotryptophan derivatives have previously been described in the literature. A number of preliminary studies indicated that Conus peptides do not contain the 5-bromotryptophan derivative. Thus, a contryphan homolog was synthesized with Trp$^4$ in the D-configuration (as in contryphan R), and in position 7, DL-6-bromotryptophan was incorporated. Synthetic peptides containing either D- or L-bromotryptophan could be resolved on HPLC and are referred to as the hydrophilic and hydrophobic components.

The more hydrophilic component of the synthetic material co-eluted with the native peptide. Indeed, even when the peptides were reduced, there was co-elution of both native and synthetic peptide, further establishing identity of natural and synthetic material. Thus, it was concluded that residue 7, which could not be assigned in amino acid sequencing, is in fact 6-bromotryptophan.

In order to confirm that the brorinated residue was in the L- and not the D-configuration, a carboxypeptidase Y digest was carried out. This enzyme is not able to cleave D-amino acid residues at the carboxy terminus of a peptide. HPLC analysis of the enzyme incubations indicated no change in the retention time of the hydrophobic peptide, which the hydrophilic peptide was consumed and a number of new species was observed. A fraction identified as BT, when isolated and measured with LSI-MS, revealed relatively intense species at m/z 283.0 and 285.0, consistent with the release of 6-bromotryptophan (the [M+H]$^+$ of bromotryptophan amino acid is 283.1 Da). Since the hydrophilic peptide which was susceptible to the enzyme co-eluted with the natural peptide, it was concluded that the bromotryptophan residue in bromocontryphan was in the L-configuration.

Example 4

Biological Activity of Bromocontryphan

The brominated peptide was designated as bromocontryphan, since it clearly differs from contryphan R by a single bromine moiety. The biological activity of bromocontryphan was examined and compared to contryphan R, as well as to the D-Br-Trp$^7$ derivative of bromocontryphan. These results are shown in Table 1. The biological activity in mammalian systems is very similar to the spectrum of activity previously observed for both contryphan R and des[Gly$^1$]contryphan R (Jimenez et al., 1996).

However, for the analog with D-Br-Trp present in place of L-Br-Trp at position 7, no biological activity was observed at twice the active dose of bromocontryphan.

TABLE 1

Biological Effects of Bromocontryplan and Analogs

| Peptide | Dose (nmol/g body wt) | Observed Effects |
|---|---|---|
| bromocontryphan | 4–7 | tail-raising, grooming, scratching tail raising, grooming, dragging of hind legs, circular motion, biting of hind paw |
|  | 10 | grooming, scratching, circular motion, dragging of hind legs, barrel rolling |
| [D-Br—Trp$^7$]bromocontryphan | 15 | none |

Example 5

Identification and Sequencing of a cDNA Clone Encoding Bromocontryphan

The primary translation product for bromocontryphan was elucidated through a cDNA cloning strategy using methods previously described (see, for example, Woodward et al., 1990; Colledge et al., 1992; and Monje et al., 1993). The relevant clones were identified from a *Conus radiatus* venom duct cDNA library that was prepared as described above. Once the clones were isolated, both strands were sequenced.

The precursor sequence for bromocontryphan determined by this strategy from the *Conus radiatus* venom duct library is shown in Table 2. The mature peptide is encoded at the extreme C-terminal end of the predicted prepropeptide precursor containing 63 amino acids. The mature peptide is produced following cleavage between residues 54 and 55. As expected, the bromotryptophan residue is encoded in the mRNA by the codon for tryptophan.

TABLE 2 cDNA Sequence of Clone Encoding Contryphan/Bromocontryphan

| met | gly | lys | leu | thr | ile | leu | val | leu | val | ala | ala | val | leu | leu | ser | ala | gln |
|---|---|---|---|---|---|---|---|---|---|---|---|---|---|---|---|---|---|
| ATG | GGG | AAA | CTG | ACA | ATA | CTG | GTT | CTT | GTT | GCT | GCT | GTC | CTG | TTG | TCG | GCC | CAG |

| val | met | val | gln | gly | asp | gly | asp | gln | pro | ala | asp | arg | asn | ala | val | pro | arg |
|---|---|---|---|---|---|---|---|---|---|---|---|---|---|---|---|---|---|
| GTC | ATG | GTT | CAA | GGT | GAC | GGA | GAT | CAA | CCT | GCA | GAT | CGT | AAT | GCA | GTG | CCA | AGA |

| asp | asp | asn | pro | gly | gly | ala | ser | gly | lys | phe | met | asn | val | leu | arg | arg | ser |
|---|---|---|---|---|---|---|---|---|---|---|---|---|---|---|---|---|---|
| GAC | GAT | AAC | CCA | GGT | GGA | GCG | AGT | GGA | AAG | TTC | ATG | AAT | GTT | CTA | CGT | CGG | TCT |

TABLE 2-continued cDNA Sequence of Clone Encoding Contryphan/Bromocontryphan

| gly | cys | pro | trp | glu | pro | trp | cys | gly | (SEQ ID NO:20) |
|-----|-----|-----|-----|-----|-----|-----|-----|-----|----------------|
| GGA | TGT | CCG | TGG | GAA | CCT | TGG | TGT | GGC | TGA (SEQ ID NO:19) |

Thus, it is presumed that the polypeptide precursor for bromocontryphan has a normal L-tryptophan after the primary translation event. A modification system then specifically brominates $Trp^7$ of bromocontryphan (most probably this modification takes place before the mature peptide is proteolytically cleaved from the precursor) to a 6-bromo-L-tryptophan residue. The selectivity in the bromination suggests that there may be a modification-signaling sequence to direct the tryptophan-brominating enzyme to a specific tryptophan residue. The sequence of a cDNA encoding another bromo-tryptophan conopeptide, the bromosleeper peptide, of Conus radiatus has also been determined. No amino acid homolgy is seen between the mature peptides, but in the prepropeptide precursor, there is a 5-amino-acid sequence, NVXRR, where X is L or I (SEQ ID NO:21), which shows substantial sequence identity (the sequence underlined in Table 2).

Example 6

Methods Relating to Bromoheptapeptide and Bromsleeper Peptide

Reagents. DIC (Chem-Impex International, Wood Dale, Ill.); DCM (Fisher Scientific, Pittsburgh, Pa.); Boc-Ala—OH, Boc-Cys(Mob)—OH, Boc-Gln(Xnt)—OH, Boc-Gly—OH, pGlu—OH, Boc-Thr(OBzl)-)OH and Boc-Ala—OH (Bachem, Torrance, Calif.); D,L-6-bromotryptophan (Biosynth A.G., Staad, Switzerland); D,L-5-bromotryptophan (synthesized as described by Porter et al., 1987); acetyl chloride (99+%), anisole, ascorbic acid, Hexyl Alcohol (98%), HOBt, iodine and piperidine (Aldrich Chemical Co., Milwaukee, Wis.), DIEA (Fisher Scientific, Pittsburgh, Pa.); TBTU and N-methylpyrrolidone (Advanced Chemtech, Louisville, Ky.); HF (Matheson Gas Prod., Cucamonga, Calif.); TFA (Halocarbon Prod. Corp., River Edge, N.J.); ether, acetonitrile and acetic acid (Mallincrodt, Baker Inc., Paris, Ky.); methanol (Burdick and Jackson Division, Muskegon, Mich.); TCEP (synthesized by the method of Burns et al., 1991); iodoacetamide, EDTA, guanidine hydrochloride, hepes, sodium carbonate, 4-vinyl pyridine, tris- HCl and tris base (Sigma, St. Louis, Mo.); β-mercaptoethanol (Pierce, Rockford, Ill.); α-chymotrypsin, aminopeptidase-M, carboxypeptidase-Y, endoproteinase lys-C, endoproteinase asp-N and pyroglutamate aminopeptidase (Boehringer Mannheim, Indianapolis, Ind.).

Crude Venom: The crude venom was obtained from Conus imperialis and Conus radiatus by dissection of the venom duct gland and stored at -70° C.

Peptide Purification: Pooled venom was diluted with 0.1% aqueous TFA and injected onto a reverse phase high performance liquid chromatography (HPLC) using a Vydak $C_{18}$ column (10×250 mm, 5 μm particle size, Rainin) and eluted with a linear gradient of acetonitrile in 0.085% TFA at 5 mL/min. The HPLC apparatus consisted of HPXL pumps and either a Dynamax model UVI or UV-DII detector (Rainin, Woburn, Mass.). Subsequent purification steps utilized a $C_{18}$ Microsorb or $C_{18}$ Vydac column, 4.6×250 mm, 5 μm particle size (Rainin). The effluents were monitored at 220 nM. Peaks were collected and aliquots were assayed for activity.

Bioassays: Biological activity of both the heptapeptide and the bromosleeper peptide was assayed by intracranial and intraperitoneal injection in mice (9–22 days old), as described by Clark and Olivera (1981). Aliquots of peptide samples were lyophilized and suspended in normal saline solution, then injected into mice using a 0.3 mL syringe with a 29-gauge needle. Twenty μL volumes were injected intracranially, and 50 μL volumes were injected intraperitoneally. Each control mouse was injected with an equal volume of normal saline solution containing dissolved residue of lyophilized column buffer. After injections, the mice were placed in cages for observation.

Enzyme Hydrolysis. (i) PAP hydrolysis: The bromoheptapeptide was incubated in a 0.1M $Na_2CO_3$ solution with pyroglutamate aminopeptidase (1:1; enzyme:substrate) at 37° C. for 17 hours. (ii) Endoproteinase Lys-C hydrolysis: Fragments of the pyridylethylated sleeper peptide were generated by digestion with endoproteinase Lys-C. The peptide was incubated with the enzyme in a total volume of 50 μL (25 mM sodium bicarbonate buffer, pH 8.5, 10% acetonitrile) at 37° C. for 16 hours. The reaction was stopped by addition of 25 μL of acetonitrile and 5 μL of 10% TFA, and digest purified with HPLC. (iii) Endoproteinase Asp-N hydrolysis: Fragments of pyridylethylated sleeper peptide were generated by digestion with endoproteinase Asp-N. The peptide was incubated with the enzyme in a total volume of 50 μL (25 mM potassium phosphate buffer, pH 8.0, 10% acetonitrile) at 37° C. for 19 hours. The reaction was stopped by addition of 25 μL of acetonitrile and 5 μL of 10% TFA, and the digest purified with HPLC. (iv) Aminopeptidase-M hydrolysis: Synthetic 1–4 bromosleeper N-terminal fragment (100 pmol) was incubated in 100 μL of 100 mM Hepes solution with 20 mU of aminopeptide-M at 24° C., and the reaction monitored with HPLC at 24 hours and 4 day time points.

Chemical Modifications: (i) Esterification: Esterification of the N-terminal (1-4) fragment of the bromosleeper peptide with acidic hexanol, prepared from acetyl chloride and hexyl alcohol, was carried out as outlined by Falcik and Maltby (1989). (ii) Reduction and Alkylation: The bromoheptapeptide was reduced with 10 mM TCEP in 200 mM sodium acetate buffer (pH 5.0) and alkylated with iodoacetamide in 30 mM Tris base (pH 10.0) containing 2 mM EDTA at RT as described by Gray (1993). The bromosleeper peptide was reduced and alkylated by either of two methods. In method 1, the peptide was dissolved in 250 mM Tris-HCl, 6M guanidine hydrochloride and 2 mM EDTA (pH 7.5), reduced with a 10% solution of β-mercaptoethanol in DI $H_2O$ at RT and alkylated in the dark with a 20% solution of 4-vinyl pyridine in ethanol. With method 2, the peptide was reduced with TCEP and alkylated with 4-vinyl pyridine as describedby Shon et al. (1994).

Chemical sequence and Amino acid analyses: Automated chemical sequence analysis was performed on a 477A Protein Sequencer (Applied Biosystems, Foster City, Calif.). Amino acid analysis was carried out using pre-column derivatization. Approximately 500 pmol of the bromoheptapeptide was sealed under vacuum with concentrated HCl, hydrolyzed at 110° C. for 24 hours, lyophilized and then derivatized with o-phthalaldehyde. The derivatized amino acids were then analyzed with HPLC.

Mass Spectrometry: Matrix assisted laser desorption (MALD; Hillenkamp et al., 1993) mass spectra were measured using a Bruker REFLEX (Bruker Instruments Inc., Bremen, Germany) time-of-flight (Cotter, 1989) mass spectrometer fitted with a gridless reflectron and a $N_2$ laser and a 100 MHz digitizer. An accelerating voltage of +31 kV and a reflector voltage of between 1.16–30 kV were employed for the post-source decay FAST (Spengler et al., 1992) measurements. The sample (in 0.1% aqueous TFA) was applied with α-cyano-4-hydroxycinnamic acid. Liquid secondary ionization (LSI; Barber et al., 1982) mass spectra were measured using a Jeol HX110 (Jeol, Tokyo, Japan) double-focusing mass spectrometer operated at 10 kV accelerating voltage. The sample (in 0.1% aqueous TFA and 25% acetonitrile) was mixed in a glycerol, 3-nitrobenzyl alcohol matrix (1:1) and analyzed with either magnetic or electric field scans. The spectra were calibrated using $[Cs(CsI)_n]^+$ cluster ions. The LSIMS spectra were measured at nominal resolutions of either 1,000 or 3,000. Electrospray mass spectra were measured using an LCQ (Finnigan MAT, San Jose, Cailf.) ion trap mass spectrometer. The samples (in 0.1% aqueous TFA) were analyzed by direct infusion with (bromoheptapeptide) or without (N-terminal 1–4 fragment of the bromosleeper peptide) the addition of 20% acetic acid (6:1) solution. The mass accuracy was typically better than: 1,000 ppm for the time-of-flight instrument in the linear mode, 220 ppm for the time-of-flight instrument in the reflectron mode and the ion trap instrument, and 50 ppm for the double-focusing mass spectrometer. It should be noted that when analyzing Gla containing peptides with time-of-flight mass spectrometers, decarboxylation can significantly reduce the mass accuracy below these levels (Nakamura et al., 1996).

Synthesis of the bromoheptapeptide: The synthesis was carried out manually on an MBHA resin using DIC as coupling reagent, with the Boc-protection strategy in DCM with the exception of the introduction of the Fmoc-D,L-6-bromotyyptophan or Fmoc-D,L-5-bromotryptophan. The MBHA resin was prepared at The Salk Institute, with a substitution of 0.5 mM/g. The D,L-6-bromotryptophan and D,L-5-bromotryptophan were derivatized to Fmoc-D,L-6-bromotryptophan and Fmoc-D,L-5-bromotryptophan, respectively. In the case of the Fmoc-D,L-6 bromotryptophan mediated coupling, HOB/DIEA was used with TBTU in N-methylpyrrolidone, followed by the deprotection of the Fmoc group with 20% piperidine in NMP. Four-fold excess of amino acid derivatives were used in the coupling reactions with the exception of the D,L-6-bromotryptophan where a 10% excess was used. The efficiency of the coupling reactions was checked using the Kaiser-ninhydrin test. The dried peptide-resin (1.28 g) was treated with 15 mL of HF in the presence of 1.5 mL of anisole at 0° C. for 1.5 hours. After the evaporation of HF, a first extraction was carried out with ether (3×100 mL) and a second extraction with 0.1% aqueous TFA and 60% acetonitrile (3×50 mL). Purification of the crude reduced product on analytical HPLC indicated two major components whose measured mass (MALD-MS) were consistent with the calculated peptide mass. The extract of the crude peptide (approximately 150 mL) was diluted with 500 mL of acetic acid, mixed vigorously and titrated with iodine in methanol (1%) until the color of the solution remained amber for 10 minutes. The excess of iodine was eliminated with a 5% ascorbic acid solution. The volume was reduced by evaporation to 70 mL and the residue diluted with 430 mL of TEAP 2.25 pH buffer. Acetonitrile was added (approximately 20 mL) until the opalescent liquid turned clear.

The crude bromoheptapeptide solution was clarified by the addition of acetonitrile (50 mL) and loaded on a 45×320 mm column packed with Vydac $C_{18}$ 15–20 μm particles and eluted with a Waters PrepLC/System 500A equipped with gradient controller, Waters Model 450 Variable Wavelength Detector and Waters 1000 PrepPack cartridge chamber in 0.1% aqueous TFA, using a gradient of 60% acetonitrile in 0.1% aqueous TFA. Fractions (50 mL) were collected manually. Two components were isolated, one of them at approximately 16% acetonitrile, the other at approximately 22% acetonitrile. The collected fractions of the first component (1,300 mL) were diluted with the same volume of 0.1% aqueous TFA and reloaded onto the equilibrated preparative HPLC column. One major component was collected at approximately 22% acetonitrile and lyophilized (34.8 mg, purity based on HPLC 99%, based on CZE 97%). The collected fractions of the second component (700 mL) were purified as above. The major component was collected at approximately 26% acetonitrile and lyophilized (28.9 mg, purity based on HPLC 99%, based on CZE 97%). LSI-MS measurement of both components resulted in an intense species at m/z 852.2 consistent with the calculated monoisotopic $[M+H]^+$ mass of 852.17 Da.

Synthesis of bromosleeper N-terminal (1-4) fragment: The synthesis was initiated on Boc-Ile-CM-resin (300 mg), prepared at The Salk Institute (1% crosslink, 200–400 mesh, substitution 0.71 mmol/g). The coupling reactions were carried out manually using the Boc/TFA protocol with DIC in the case of coupling Boc-Thr(OBzl)—OH and Boc-Ala—OH (three equivalents) in DCM. The N-terminal residue D,L-6-bromotryptophan was introduced as the N-Fmoc-D,L-6-bromotryptophan derivative (two equivalents). The coupling was mediated with DIEA/HOBt and TBTU, and was used as condensing agent in NMP. Each coupling reaction was completed within two hours and checked using the Kaiser-ninhydrin test. The N-terminal Fmoc-group was removed with 20% piperidine/nMP in 2×10 minutes. The weight of the washed and dried resin was 390 mg (weight gain 90 mg). The dried deprotected peptide-resin (390 mg) was treated with 4 mL of HF in the presence of 0.4 mL of anisole at 0° C. for 1.5 hours. After the evaporation of HF, a first extraction was carried out with ether (3×25 mL) and a second extraction with 0.1% TFA and 60% acetonitrile (3×15 mL) in water. The fingerprint of the crude product on analytical HPLC indicated two major components (diastereomer of the L or D-6-bromotryptophan tetrapeptide) with observed masses (MALDI-MS) which were consistent with the calculated peptide mass.

The purification of bromosleeper N-terminal (1-4) fragment involved evaporation of 25% of the aqueous extract (rotavap 38° C. water-bath). The solid residue was redissolved in 3.0 mL of 0.1% aqueous TFA, 20% acetonitrile buffer and loaded in 0.5 mL portions to a semi-preparative column. The fractions were collected manually and checked by analytical HPLC. The first pooled and lyophilized fractions resulted in 8.8 mg of peptide which was 99.9% pure by CZE, and the second fraction resulted in 7.8 mg pure optical isomer tetrapeptide with 98% purity by CZE. LSI-MS measurement of both fractions resulted in an intense species at m/z 568.2, which compared closely with calculated $[M+H]^+$ monoisotopic mass of 568.18 Da.

Peptide Characterization: (i) Co-elution of natural and synthetic bromoheptapeptide. Reverse-phase HPLC co-elution experiments of natural and synthetic bromoheptapeptide were carried out with a Vydac $C_{18}$ (5 μm, 300 Å particle size) 2.1×150 mm column at a flow rate of 200 μL/min. Volatile buffers (0.055% aqueous TFA and acetonitrile) were used, and effluent was monitored at 210, 254 and 280 nM with a HP1090 (Hewlett Packard, Wilmington, Del.). (ii) Determination of L- vs. D-6 bromotryptophan containing bromoheptapeptide: The two purified peptides (corresponding with either the D- or L-isomers of 6-bromo-tryptophan) were reduced and alkylated. The HPLC purified reduced and alkylated peptides were lyophilized and redissolved in 250 mM Tris base (pH 8.5) and incubated with α-chymotrypsin (1:40, 1:10 and 1:5; enzyme:substrate) for up to nine days. The progress of the reaction was monitored with HPLC and MALD-MS. (iii) Co-elution of natural and synthetic bromosleeper peptide N-terminal (1-4) fragment: Approximately equal amounts of the endoproteinase asp-N-digested N-terminal fragment of the bromosleeper peptide and the synthetic peptide Xaa-Ala-Thr-Ile—OH (SEQ ID NO:22) were mixed (where Xaa= bromotryptophan). The mixture was applied onto a $C_{18}$ analytical column and eluted at 1 mL/min using a gradient of acetonitrile in 0.085% TFA. A similar amount of the synthetic was analyzed on HPLC under the same conditions. (iv) Determination of L- vs. D-6-bromotryptophan in bromosleeper peptide N terminal (1-4) fragment: An aliquot (10 μL) of each synthetic peptide (1 mM) was lyophilized, redissolved in 100 mM Hepes (pH 7.5), and incubated with aminopeptidase-M (1:40; enzyme:substrate) for up to four days. The progress of the reaction was monitored with HPLC. The product of the aminopeptidase-M reaction was co-injected with the racemic mixture of 6-bromotryptophan or with the racemic mixture of 5-bromotryptophan.

Example 7

Purification and Characterization of Bromoheptapeptide

The heptapeptide containing L-6 bromotryptophan was isolated from venom of predatory *Conus imperialis*. The bromoheptapeptide was purified from a side fraction isolated during the purification of another unrelated peptide α-conotoxin IMI (McIntosh et al., 1996). Interest in this sample was initially stimulated after scanning fractions present in the crude venom for novel peptides based on the intact mass (Craig et al., 1994), rather than biological activity. MALD-MS analysis of the purified fraction indicated species at m/z 853, 855, 875 and 879 Da. In order to obtain higher mass resolution without sacrificing sensitivity, this sample was analyzed with electrospray ionization and an ion trap mass spectrometer. Several relatively intense species were observed with 2 Da separation at m/z 835.9 and 837.9, m/z 853.1 and 855.1, and m/z 875.2 and 877.2, which are referred to as doublets. These doublets could be clearly resolved using a zoom scan (e.g., m/z 853.1 and 855.1). The separation of approximately 22 Da between m/z 853.1 and 875.2 (and also between m/z 855.1 and 877.2) suggested competitive $[M+H]^+$ and $[M+Na]^+$ formation (M=852). Accordingly, the m/z 835.9 and 837.9 doublets were attributed to a loss of $NH_3$ from the protonated molecule ion. The presence of the doublets was characteristic of a molecule containing a single $^{79}Br$ or $^{81}Br$ atom. This pattern of isotopomers is quite distinctive, since these isotopes are separated by two Da and have approximately equal natural abundance, and this characteristic doublet was observed from both the synthetic 5- and 6-bromotryptophan amino acids. Accurate mass analysis using LSI on a magnetic sector instrument was used to determine masses of m/z 853.19 and 855.20 for the $[M+H]^+$ doublets. It was deduced that the peptide was N-terminally blocked with pyroglutamic acid from initial chemical sequencing measurements and the shift in chromatographic retention time following treatment with pyroglutamate aminopeptidase.

Automated Edman degradation analysis after pyroglutamate aminopeptidase treatment resulted in the sequence: Cys-Gly-Gln-Ala-Xaa-Cys, where Xaa indicates a blank cycle (SEQ ID NO:23). Amino acid analysis confirmed the presence of one mole ratio of glycine and alanine to two mole ratios of glutamate and cysteine. A major component of the hydrolysate-eluted 0.7 minute after the expected retention time of derivatized tryptophan but 2.2 minutes before the expected retention time of derivatized arginine. After reduction and alkylation of the sample with iodoacetamide (to form the Cys(Cam) derivative which has a residue mass of 160 Da), MALD-MS analysis revealed two sets of doublets at m/z 991 and 993 and m/z 1007 and 1009, separated by 16 Da. These species were interpreted as the $[M'+Na]^+$ and $[M'+K]^+$ of the reduced and alkylated peptide (M'=968 Da). The shift in mass after reduction and alkylation (M'−M=968−852=116 Da) was consistent with the presence of two cysteine residues. Other species observed were interpreted as fragment ions (e.g., m/z 788 corresponds with the postsource decay $b_6$ fragment ion). The post-source decay FAST spectrum of the reduced and alkylated product were measured at low, medium and high laser power fluences. The position of the monoisotopic $[M'+H]^+$ =969 was noted, although only the cationized intact ions were observed. Three fragment ions which were observed above the background noise level in the low power spectrum at m/z 793.1, 528.1 and 456.6 were also observed at varying intensities at medium and high laser power. Based on the mass differences between the parent and the successive fragments (186.9, 265.0 and 71.5 Da), these ions were interpreted as corresponding to N-terminal fragments differing in mass by Cys(Cam), X and Ala, where X=265 Da. It was concluded that these three fragment ions ($b_6$, $b_5$ and $b_4$) encompass the blank observed in the chemical sequence data. Based on these results, it was deduced that the sixth amino acid was hydrophobic, absorbed intensely at 280 nM and had a mass of 265 Da. The following sequence was proposed: $Xaa_1$-Cys-Gly-Gln-Ala-$Xaa_2$-Cys—$NH_2$, where $Xaa_1$=pyroglutamic acid and $Xaa_2$=bromotryptophan (SEQ ID NO:2). The calculated $[M+H]^+$ for the monoisotopic mass of the bromoheptapeptide (853.176 Da) was consistent with the measured m/z of 853.19.

Example 8

Chemical Synthesis of Bromoheptapeptide

Assignment of bromotryptophan was confirmed by total chemical synthesis of the bromoheptapeptide. The synthesis of bromoheptapeptide using a racemic mixture of the D- and L- forms of 6-bromotryptophan resulted in two diastereomeric peptides, one containing the D-configuration 6-bromotryptophan at position 6, the other containing the L-configuration 6-bromotryptophan at position 6. HPLC purification of the crude synthesis product indicated the presence of a hydrophobic and a hydrophilic species, both of which contained the characteristic doublet at m/z 853.2 and 855.2 consistent with the native bromoheptapeptide based on LSI-MS analysis. The separation of the peptides containing a D- vs. an L- amino acid by reverse phase HPLC exploits structural differences that attend chiral inversion at the ca atom. The hydrophilic isomer co-eluted with the natural peptide on HPLC). The susceptibility of the modified tryptophan residue toward enzymatic hydrolysis after reduction and alkylation of the cysteine residues was determined by incubation of the synthetic peptide with α-chymotrypsin. The hydrophilic isomer was observed to hydrolyze when incubated with a 1:10 enzyme to substrate ratio within two days, whereas the hydrophobic isomer underwent no hydrolysis at this enzyme to substrate ratio when incubated for nine days. The intact mass and isotopomer distribution for the chymotrypsin hydrolyzed fragment analyzed with LSI-MS corresponded with the calculated mass for the reduced and alkylated 1-6 bromoheptapeptide fragment (Xaa$_1$-Cys(Cam)-Gly-Gln-Ala-Xaa$_2$—OH, where Xaa$_1$ is Gla and Xaa$_2$ is bromotryptophan (SEQ ID NO:24); calculated monoisotopic mass for the [M+H]$^+$ is 810.19 Da, observed m/z 810.2.

Example 9

Purification and Characterization of Bromosleeper Peptide

A novel "sleeper" peptide which induces a sleep-like state in mice was purified from *Conus radiatus* venom. A family of peptides which elicit a sleep-like state in mice, the conantokins, have previously been described from Conus venoms. The peptide isolated from *Conus radiatus* was very different from the conantokins with respect to activity profile. Whereas the conantokins cause sleep when injected intracranially in very young mice (<2 weeks old) and hyperactivity in older mice (>3 weeks old), the new peptide induced sleep in mice of both age groups. A summary of the in vivo effect of the purified peptide is shown in Table 3. It is obviously more potent in 9-day-old mice than in the older mice; the effective dose is lower, the onset time is shorter, and the duration of sleep is longer in younger mice.

TABLE 3

Biological Effects of Bromosleeper Peptide

| Dose | Observed Effects in Mice | | |
|---|---|---|---|
| pmol/g body weight | 9 day old | 17 day old | 22 day old |
| 10–15 | slept ≈ 1 hr | not tested | not tested |
| 40–50 | slept > 10 hr | lethargic/drowsy after ≈ 15 min | lethargic/drowsy after ≈ 19 min |
| 70 | slept > 24 hr | lethargic/drowsy after ≈ 11 min slept ≈ 4 hr | not tested |
| 100 | not tested | not tested | |

MALD-MS analysis of the purified fraction measured in the linear mode indicated a broad species at m/z 3884 Da, in contrast to the measurement in the reflectron mode of m/z 3729 Da. LSI-MS analysis of the same sample indicated a species at m/z 3916.4. These results suggested that the peptide contained a number of Gla residues (Nakamura et al., 1996). Chemical sequencing after reduction and pyridylethylation of the cysteine residues gave no regular PTH derivative at cycle one, but an intense signal for alanine at cycle two, followed by normal repetitive recovery. Weak signals were also observed at positions 6, 8 and 9. Endoproteinase Asp-N hydrolysis of the bromo sleeper peptide generated three major fractions which, when submitted to chemical sequence analysis, revealed the following sequences: (i) Xaa-Ala-Thr-Ile (SEQ ID NO:25), (ii) Asp-Xaa-Cys-Xaa-Xaa-Thr-Cys-Asn-Val-Thr-Phe-Lys-Thr-Cys-Cys-Gly-Hyp-Hyp-Gly(SEQ ID NO:26), and (iii) Asp-Trp-Gln-Cys-Val-Xaa-Ala-Cys-Pro-Val (SEQ ID NO:27), where Xaa indicates a blank cycle. Endoproteinase Lys-C hydrolysis generated two fragments which, after mass spectrometry and chemical sequence analysis, could be used to deduce the connectivity of the 3 Asp-N fragments as (i) 1-4; (ii) 5-23 and (iii) 24-33. Based on mass spectrometric analysis of the Asp-N fragments 5-23 and 24-33, the weak signals at 6, 8, 9 and 29 were interpreted as Gla residues. The accurate mass of the 24-33 fragment indicated that the C-terminus of the peptide was in the free acid form. A strong UV absorption was noted at 280 nm for both the intact peptide and the N-terminal fragment characteristic of an indole group. Although it was reasonable to expect such absorption from the intact peptide which contains tryptophan in the case of the 1-4 fragment this adsorption was attributed to the residue in position 1. Electrospray ionization ion trap mass spectral analysis of the N-terminal 1-4 fragment revealed a weak (but constant) signal which, when accumulated over several minutes, resulted in a doublet of peaks at m/z 568.1 and 570.1. LSI-MS analysis of the N-terminal 1-4 fragment (after esterification with hexanol to optimize the sensitivity of LSI analysis; resulting in addition of 84 Da) also resulted in a weak signal where a double at m/z 652.27 and 654.26 could be observed which was not present when the matrix alone was analyzed. The similarity between the isotopomer intensities of the doublet observed for the fragment and that observed for the bromoheptapeptide and the synthetic bromotryptophan amino acids was noted. The properties of the modified amino acid were consistent with the presence of bromotryptophan; e.g., the observed m/z of 652.27 was consistent with the calculated monoisotopic mass for the [M+H]$^+$ of the 1-4 fragment Trp-A-T-I-C$_6$H$_{12}$ (652.271 Da). The following sequence was proposed: Xaa$_1$-Ala-Thr-Ile-Asp-Xaa$_2$-Cys-Xaa$_2$-Xaa$_2$-Thr-Cys-Asn-Val-Thr-Phe-Lys-Thr-Cys-Cys-Gly-Xaa 3-Xaa3-Gly-Asp-Trp-Gln-Cys-Val-Xaa2-Ala-Cys-Pro-Val-OH, where Xaa$_3$=hydroxyproline, Xaa$_2$=Gla and Xaa$_1$=bromotryptophan (SEQ ID NO:3).

Example 10

Chemical Synthesis of 1-4 N-Terminal Fragment of Bromosleeper Peptide

After synthesis of the bromosleeper peptide 1-4 N-terminal fragment with a racemic mixture of the D- and L- forms of 6-bromotryptophan, a hydrophobic and hydrophilic peptide isomer were purified. LSI-MS analysis of both the hydrophobic and hydrophilic peptide isomer resulted in mass spectra consistent with that of the native 1-4 bromosleeper fragment. The hydrophilic isomer was found to co-elute with the natural peptide on HPLC. Susceptibility of bromotryptophan residue toward enzymatic hydrolysis was determined by incubation of the synthetic peptide with aminopeptidase-M. The hydrophilic isomer was observed to hydrolyze within 24 hours, whereas the hydrophobic isomer underwent no hydrolysis under the same conditions or when incubated for four days. The bromotryptophan amino acid released from the hydrophilic isomer co-eluted on HPLC with the racemic mixture of 6-bromotryptophan but did not co-elute with the racemic mixture of 5-bromotryptophan.

Example 11

Identification and Sequencing of a cDNA Clone Encoding Bromosleeper Peptide

The primary translation product for bromosleeper peptide was elucidated through a cDNA cloning strategy using methods previously described (see, for example, Woodward et al., 1990; Colledge et al., 1992; and Monje et al., 1993). The relevant clones were identified from a *Conus radiatus* venom duct cDNA library that was prepared as described above. Once the clones were isolated, both strands were sequenced.

The precursor sequence for bromosleeper peptide determined by this strategy from the *Conus radiatus* venom duct library is shown in Table 4. The mature peptide is encoded at the extreme C-terminal end of the predicted prepropeptide precursor containing 78 amino acids. The mature peptide is produced following cleavage between residues 45 and 46. As expected, the bromotryptophan residue is encoded in the mRNA by the codon for tryptophan.

(1995), using the maximal electroshock, subcutaneous pentylenetetrazol (Metrazol) seizure threshhold and threshold tonic extension test. Bromosleeper peptide is found to have anticonvulsant activity.

It will be appreciated that the methods and compositions of the instant invention can be incorporated in the form of a variety of embodiments, only a few of which are disclosed herein. It will be apparent to the artisan that other embodiments exist and do not depart from the spirit of the invention. Thus, the described embodiments are illustrative and should not be construed as restrictive.

TABLE 4 cDNA Sequence of Clone Encoding Bromosleeper Peptide

| met | ser | gly | leu | gly | phe | met | val | leu | thr | leu | leu | leu | leu | thr | phe | met | ala |
|---|---|---|---|---|---|---|---|---|---|---|---|---|---|---|---|---|---|
| ATG | TCG | GGA | TTG | GGA | TTC | ATG | GTG | CTA | ACC | CTT | CTA | CTT | CTT | ACG | TTC | ATC | GCA |
| thr | ser | his | gln | asp | arg | gly | glu | lys | gln | ala | thr | gln | arg | his | als | ile | <u>asn</u> |
| ACC | AGT | CAT | CAG | GAT | AGA | GGA | GAG | AAG | CAG | GCG | ACG | CAA | AGG | CAC | GCA | ATC | <u>AAT</u> |
| <u>val</u> | <u>ile</u> | <u>arg</u> | <u>arg</u> | arg | leu | ile | thr | arg | trp | ala | thr | ile | asp | glu | cys | glu | glu |
| <u>GTC</u> | <u>ATA</u> | <u>AGG</u> | <u>AGA</u> | AGA | TTA | ATC | ACT | CGC | TGG | GCA | ACA | ATT | GAC | GAG | TGC | GAA | GAG |
| thr | cys | asn | val | thr | phe | lys | thr | cys | cys | gly | pro | pro | gly | asp | trp | gln | cys |
| ACA | TGC | AAC | GTG | ACG | TTT | AAG | ACC | TGC | TGC | GGT | CCA | CCT | GGA | GAT | TGG | CAA | TGT |
| val | glu | ala | cys | pro | val | (SEQ ID NO:29) | | | | | | | | | | | |
| GTC | GAA | GCA | TGC | CCC | GTG | TAG | (SEQ ID NO:28) | | | | | | | | | | |

As noted above in Example 5, no amino acid homolgy is seen between the mature bromosleeper peptide and the bromocontryphan peptide, but in the prepropeptide precursor, there is a 5-amino-acid sequence, NVXRR, where X is L or I (SEQ ID NO:21), which shows substantial sequence identity (the sequence underlined in Table 4).

Example 12

Purification and Characterization of Sigma Conotoxin

A novel peptide which targets the serotonin $5HT_3$ receptor was purified from *Conus geographus* venom using similar techniques to those described above. This peptide was characterized using similar techniques to those described above. The peptide named sigma conotoxin has the structure: Gly-Cys-Thr-Arg-Thr-Cys-Gly-Gly-$Xaa_1$-Lys-Cys-Thr-Gly-Thr-Cys-Thr-Cys-Thr-Asn-Ser-Ser-Lys-Cys-Gly-Cys-Arg-Tyr-Asn-Val-His-Pro-Ser-Gly-$Xaa_2$-Gly-Cys-Gly-Cys-Ala-Cys-Ser, where $Xaa_1$ is Hyp and $Xaa_2$ is 6-bromo-L-tryptophan (SEQ ID NO:10).

Example 13

In vivo Activity of Bromosleeper Peptide in Frings Audiogenic Seizure Susceptible Mice In vivo anticonvulsant activity of bromosleeper peptide is analyzed in Frings audiogenic seizure susceptible mice as described by White et al. (1992). Bromosleeper peptide is seen to have activity in this model.

Example 14

In vivo Activity of Bromosleeper Peptide in CF No. 1 Mice

In vivo anticonvulsant activity of bromosleeper peptide is analyzed in CF No. 1 mice as described by White et al.

LIST OF REFERENCES

Abiko, H. et al. (1986). Protective effect of phenytoin and enhancement of its action by combined administration of mannitol and vitamin E in cerebral ischemia. *Brain Res.* 38:328–335.

Aldrete, J. A. et al. (1979). Effect of pretreatment with thiopental and phenytoin on postischemic brain damage in rabbits. *Crit. Care Med.* 7:466–470.

Ascher, P. and Nowak, L. (1986). Calcium permeation of the channels activated by N-methyl-D-aspartate (NMDA) in mouse central neurons. *J Physiol.* 377:35p.

Barber, M. et al. (1982). *Anal. Chem.* 54:645A–657A.

Bliss, et al. (1993). *Nature* 361:31-.

Bodansky et al. (1966). *Chem. Ind.* 38:1597–98.

Bowyer, J. F. (1982). Phencyclidine inhibition of the rate of kindling development. *Esp. Neural* 75:173–175.

Burns, J. A. et al. (1991). *J Org. Chem.* 56:2648–2650.

Chandler, P. et al. (1993). Polyamine-like Actions of Peptides Derived from Contryphan-G, an N-methyl-D-aspartate (NMDA) Antagonist. *J Biol. Chem.* 268:17173–17178.

Clark, C. and Olivera B. (1981). *Toxicon* 19:691–699.

Cline, H. T. et al. (1987). N-Methyl-D-aspartate receptor antagonist desegregates eye-specific stripes. *Proc. Natl. Acad. Sci. USA* 84:4342–4345.

Colledge, C. J. et al. (1992). *Toxicon* 30:111–1116.

Collinridge, G. L. et al. (1983). Excitatory amino acids in synaptic transmission in the Schaffer collateral-commissural pathway of the rat hippocampus. *J. Physiol.* 334:34–46.

Cotter, R. J. (1989). *Biomed. Mass Spectrom.* 18:513–532.

Craig, A. G. et al. (1994). *In Techniques in Protein Chemistry VI*, J. W. Crabb Eds., Academic Press, San Diego, Calif., pp31–38.

Cruz, L. J. at al. (1976). *Verliger* 18:302–308.

Cruz, L. J. et al. (1987). *Conus geographus* toxins that discriminate between neuronal and muscle sodium channels. *J. Biol. Chem.* 260:9280–9288.

Doyle, D. D. et al. (1993). Divalent cation competition with [$^3$H]saxitoxin binding to tetrodotoxin-resistant and -sensitive sodium channels. *J. Gen. Physiol.* 101:153–182.

Dudley, S. C. et al. (1995). A μ-Conotoxin-Insensitive Na$^+$ Channel Mutant: Possible Localization of a Binding Site at the Outer Vestibule. *Biophys. J.* 69:1657–1665.

Falick, A. M. and Maltby, D. A. (1989). *Anal. Biochem.* 182:165–169.

Foster, A. and Fagg, G. (1987). Taking apart NMDA Receptors. *Nature* 329:395–396.

Gray, W. R. (1993). Disulfide Structures of Highly Bridged Peptides: A New Strategy for Analysis. *Protein Science* 2:1732–1748.

Haack, J. A. et al. (1990). Contryphan-T: a gamma-carboxyglutamate containing peptide with N-methyl-d-aspartate antagonist activity. *J. Biol. Chem.* 265:6025–6029.

Harris, E. W. et al. (1984). Long-term potentiation in the hippocampus involves activation of N-methyl-D-aspartate receptors. *Brain Res.* 323:132–137.

Hillenkamp, F. et al. (1993). *Anal. Chem.* 63:1193A–1203A.

Horiki, K. et al. (1978). *Chemistry Letters* 165–68.

Jimenez, E. C. et al. (1996). *J. Biol. Chem.* 281:28002–28005.

Johnson, J. W. and Ascher, P. (1987). Glycine potentiates the NMDA response in cultured mouse brain neurons. *Nature* 325:529–531.

Johnson, K. and Jones, S. (1990). Neuropharmacology of Phencyclidine: Basic Mechanisms and Therapeutic Potential. *Ann. Rev. Pharmacol. Toxicol.* 30:707–750.

Kaiser et al. (1970). *Anal. Biochem.* 34:595.

Kapoor (1970). *J. Pharm. Sci.* 59:1–27.

Kleckner, N. W. and Dingledine, R. D. (1988). Requirement for glycine inactivation of NMDA receptors expressed in *Xenopus* oocytes. *Science* 241:835–837.

Kornreich, W. D. et al. (1986). U.S. Pat. No. 4,569,967.

Mayer, M. and Miller R. (1990). Excitatory amino acid receptors, second messengers and regulation of intracellular Ca$^{2+}$ in mammalian neurons. *Trends in Pharmacol. Sci.* 11:254–260.

Mayer, M. L. et al. (1987). Agonist- and voltage-gated calcium entry in cultured mouse spinal cord neurons under voltage clamp measured using arsenazo III. *J. Neurosci.* 7:3230–3244.

Mena, E. E. et al. (1990). Contryphan-G: a novel peptide antagonist to the N-methyl-D-aspartic acid (NMDA) receptor. *Neurosci. Lett.* 118:241–244.

McIntosh, M. et al. (1996). *J. Biol. Chem.* 269:16733–16739.

McNamara, J. O. et al. (1988). Anticonvulsant and antiepileptogenic action of MK-801 in the kindling and electroshock models. *Neuropharmacology* 27:563–568.

*The Merck Manual of Diagnosis and Therapy*, 16 Ed., Berkow, R. et al., eds., Merck Research Laboratories, Rahway, N.J., pp. 1436–1445 (1992).

*Methoden der Organischen Chemie (Houben-Weyl): Synthese von Peptiden*, E. Wunsch (Ed.), Georg Thieme Verlag, Stuttgart, Ger. (1974).

Monje, V. D. et al. (1993). *Neuropharmacology* 32:1141–1149.

Morris, R. G. M. et al. (1986). Selective impairment and blockade of long-term potentiation by an N-methyl-D-aspartate receptor antagonist, AP5. *Nature* 319:774–776.

Nakamura, T. et al. (1996). *Protein Science* 5:524–530.

Nehlig, A. et al. (1990). Effects of phenobarbital in the developing rat brain. In *Neonatal Seizures*, Wasterlain, C. G. and Vertt, P. (eds.), Raven Press, New York, pp. 285–194.

Nishiuchi, Y. et al. (1993). Synthesis of gamma-carboxyglutamic acid-containing peptides by the Boc strategy. *Int. J Pept. Protein Res.* 42:533–538.

Nowak, L. et al. (1984). Magnesium gates glutamic-activated channels in mouse central neurons. *Nature* 307:462–465.

Olivera, B. M. et al. (1984). U.S. Pat. No. 4,447,356.

Olivera, B. M. et al. (1985). Peptide neurotoxins from fish-hunting cone snails. *Science* 230:1338–1343.

Park, C. K. et al. (1988). The glutamate antagonist MK-801 reduces focal ischemia brain damage in the rat. *Ann. Neurol.* 24:543–551.

Porter, J. et al. (1987). *Int. J. Pept. Prot. Res.* 30:13–21.

Rall T. W. and Schleifer, L. S. in *Goodman and Gilman's The Pharmacological Basis of Therapeutics*, Seventh Ed., Gilman, A. G. et al., eds., Macmillan Publishing Co., New York, pp. 446–472 (1985).

Reynolds, I. J. et al. (1987). $^3$H-Labeled MK-801 binding to excitatory amino acid receptor complex from rat brain is enhance by glycine. *Proc. Natl. Acad. Sci. USA* 84:7744–7748.

Rivier, J. R. et al. (1978). *Biopolymers* 17:1927–38.

Rivier, J. R. et al. (1987). Total synthesis and further characterization of the gamma-carboxyglutamate-containing 'sleeper' peptide from *Conus geographus*. *Biochem.* 26:8508–8512.

Roberts, et al. (1983). *The Peptides* 5:342–429.

Sambrook, J. et al. (1979). *Molecular Cloning: A Laboratory Manual*, 2nd Ed., Cold Spring Harbor Laboratory, Cold Spring Harbor, N.Y.

Schroder & Lubke (1965). *The Peptides* 1:72–75, Academic Press, N.Y.

Shon, K.-J. et al. (1994). *Biochemistry* 33:11420–11425.

Simon, R. P. et al. (1984). Blockade of N-methyl-D-aspartate receptors may protect against ischemic damage in the brain. *Science* 226:850–852.

Skolnick, P. et al. (1992). Noncompetitive Inhibition of N-Methyl-D-Aspartate by Contryphan-G: Evidence for an Allosteric Interaction at Polyamines Sites. *J. Neurochem.* 59:1526–1521.

Spengler, B. et al. (1992). *Rapid Commun. Mass. Spectrom.* 6:105–108.

Stewart and Young, *Solid-Phase Peptide Synthesis*, Freeman & Co., San Francisco, Cailf. (1969).

Troupin, A. S. et al. (1986). MK-801. In *New Anticonvulsant Drugs, Current Problems in Epilepsy* 4, Meldrurn, B. S. and Porter, R. J. (eds.), John Libbey, London, pp. 191–202.

Vale et al. (1978). U.S. Pat. No. 4,105,603.

White, H. S., et al. (1992). Anticonvulsant profile of MDL 27,266: an orally active, broad-spectrum anticonvulsant agent. *Epilepsy Res.* 12:217–226.

White, H. S., et al. (1995). Experimental Selection, Quantification, and Evaluation of Antiepileptic Drugs. In *Antiepileptic Drugs*, 4th Ed., Levy, R. H., eds., Raven Press, New York, pp. 99–110.

Williams, K. et al. (1991). Modulation of the NMDA receptor by polyamines (Minireview). *Life Sci.* 48:469–498.

Wong, E. H. P. et al. (1986). The anticonvulsant MK-801 is a potent NMDA antagonist. *Proc. Natl. Acad. Sci. USA* 83:7104–7108.

Woodward, S. R. et al. (1990). *EMBO J* 9:1015–1020.

Wroblewski, J. T. et al. (1989). Glycine and D-serine act a positive modulators of signal transduction at N-methyl-D-aspartate sensitive glutamate receptors in cultured cerebellar granule cells. *Neuropharmacology* 28:447–452.

Zhou L. M., et al. (1996a). Synthetic Analogues of Contryphan-G: NMDA Antagonists Acting Through a Novel Polyamine-Coupled Site. *J. Neurochem.* 66:620–628.

U.S. Pat. No. 3,972,859 (1976).
U.S. Pat. No. 3,842,067 (1974).
U.S. Pat. No. 3,862,925 (1975).
U.S. Pat. No. 4,904,681
U.S. Pat. No. 5,061,721
U.S. Pat. No. 5,086,072
PCT Published Application WO 94/07914
PCT Published Application WO 96/11698

What is claimed is:

1. A substantially pure bromo-tryptophan conopeptide having the general formula:

$R\text{-}(Cys)_n\text{-}R^1\text{-}B\text{-}R^2\text{-}Cys\text{-}R^3$, wherein R is a peptide chain of 0 amino acids;

$R^1$ is a peptide chain of 0 amino acids;

R² is a peptide chain of 4–6 amino acids;
R³ is a peptide chain of 3–26 amino acids;
B is 6-bromo-L-tryptophan; and
n is 0,
   provided that the total length of the bromo-tryptophan conopeptide is from 6 to 45 amino acids, and pharmaceutically acceptable salts thereof.

2. A substantially pure bromo-tryptophan conopeptide having the general formula:

$$R\text{-}(Cys)_n\text{-}R^1\text{-}B\text{-}R^2\text{-}Cys\text{-}R^3,$$

wherein
R is a peptide chain of 1–2 amino acids;
R¹ is a peptide chain of 2–5 amino acids;
R² is a peptide chain of 0 amino acids;
R³ is a peptide chain of 0 amino acids;
B is 6-bromo-L-tryptophan; and
n is 1,
   provided that the total length of the bromo-tryptophan conopeptide is from 6 to 45 amino acids, and pharmaceutically acceptable salts thereof.

3. A substantially pure bromo-tryptophan conopeptide having the general formula:

$$R\text{-}(Cys)_n\text{-}R^1\text{-}B\text{-}R^2\text{-}Cys\text{-}R^3,$$

wherein
R is a peptide chain of 1–4 amino acids;
R¹ is a peptide chain of 21–31 amino acids;
R² is a peptide chain of 1–2 amino acids;
R³ is a peptide chain of 4–7 amino acids;
B is 6-bromo-L-tryptophan; and
n is 1,
   provided that the total length of the bromo-tryptophan conopeptide is from 6 to 45 amino acids, and pharmaceutically acceptable salts thereof.

4. The bromo-tryptophan conopeptide of claim 2 having the amino acid sequence Gly-Cys-Xaa₁-Xaa₂-Glu-Pro-Xaa₃-Cys, wherein Xaa₁ is Hyp or Pro, Xaa₂ is D-Trp and Xaa₃ is L-6-bromo-tryptophan (SEQ ID NO:1).

5. The bromo-tryptophan conopeptide of claim 2, wherein Xaa₁ is Hyp.

6. The bromo-tryptophan conopeptide of claim 3, wherein the carboxy terminus contains an amide group.

7. The bromo-tryptophan conopeptide of claim 1, having the amino acid sequence Xaa₁-Cys-Gly-Gln-Ala-Xaa₂-Cys, wherein Xaa₁ is Gla or Glu and Xaa₂ is 6-bromo-L-tryptophan (SEQ ID NO:2).

8. The bromo-tryptophan conopeptide of claim 7, wherein Xaa₁ is Gla.

9. The bromo-tryptophan conopeptide of claim 8, wherein the carboxy terminus contains an amide group.

10. The bromo-tryptophan conopeptide of claim 1 having the amino acid sequence Xaa₁-Ala-Thr-Ile-Asp-Xaa₂-Cys-Xaa₂-Xaa₂-Thr-Cys-Asn-Val-Thr-Phe-Lys-Thr-Cys-Cys-Gly-Xaa₃-Xaa₃-Gly-Asp-Trp-Gln-Cys-Val-Xaa₂-Ala-Cys-Pro-Val, wherein Xaa₁ is 6-bromo-L-tryptophan, Xaa₂ is Gla or Glu and Xaa₃ is Hyp or Pro (SEQ ID NO:3).

11. The bromo-tryptophan conopeptide of claim 10, wherein Xaa₂ is Gla and Xaa₃ is Hyp.

12. The bromo-tryptophan conopeptide of claim 9, wherein the carboxy terminus contains a hydroxyl group.

13. The bromo-tryptophan conopeptide of claim 3 having the amino acid sequence Gly-Cys-Thr-Arg-Thr-Cys-Gly-Gly-Xaa₁-Lys-Cys-Thr-Gly-Thr-Cys-Thr-Cys-Thr-Asn-Ser-Ser-Lys-Cys-Gly-Cys-Arg-Tyr-Asn-Val-His-Pro-Ser-Gly-Xaa₂-Gly-Cys-Gly-Cys-Ala-Cys-Ser, wherein Xaa₁ is Hyp or Pro and Xaa₂ is 6-bromo-L-tryptophan (SEQ ID NO:10).

14. The bromo-tryptophan conopeptide of claim 13, wherein Xaa₁ is Hyp.

15. The bromo-tryptophan conopeptide of claim 1 having an amino acid sequence selected from the group consisting of:
   (a) Xaa₁-Ala-Thr-Ile-Asp-Xaa₂-Cys-Xaa₂-Xaa₂-Thr-Cys, wherein Xaa₁ is 6-bromo-L-tryptophan and Xaa₂ is Gla or Glu (SEQ ID NO:4);
   (b) Xaa₁-Ala-Thr-Ile-Asp-Xaa₂-Cys-Xaa₂-Xaa₂-Thr-Cys-Asn-Val-Thr-Phe-Lys-Thr-Cys, wherein Xaa₁ is 6-bromo-L-tryptophan and Xaa₂ is Gla or Glu (SEQ ID NO:5);
   (c) Xaa₁-Ala-Thr-Ile-Asp-Xaa₂-Cys-Xaa₂-Xaa₂-Thr-Cys-Asn-Val-Thr-Phe-Lys-Thr-Cys-Cys-Gly-, wherein Xaa₁ is 6-bromo-L-tryptophan and Xaa₂ is Gla or Glu (SEQ ID NO:6);
   (d) Xaa₁-Ala-Thr-Ile-Asp-Xaa₂-Cys-Xaa₂-Xaa₂-Thr-Cys-Asn-Val-Thr-Phe-Lys-Thr-Cys-Cys-Gly-Xaa₃-Xaa₃-Gly, wherein Xaa₁ is 6-bromo-L-tryptophan, Xaa₂ is Gla or Glu and Xaa₃ is Hyp or Pro (SEQ ID NO:7);
   (e) Xaa₁-Ala-Thr-Ile-Asp-Xaa₂-Cys-Xaa₂-Xaa₂-Thr-Cys-Asn-Val-Thr-Phe-Lys-Thr-Cys-Cys-Gly- Xaa₃-Xaa₃-Gly-Asp-Trp-Gln-Cys, wherein Xaa₁ is 6-bromo-L-tryptophan, Xaa₂ is Gla or Glu and Xaa₃ is Hyp or Pro (SEQ ID NO:8); and
   (f) Xaa₁-Ala-Thr-Ile-Asp-Xaa₂-Cys-Xaa₂-Xaa₂-Thr-Cys-Asn-Val-Thr-Phe-Lys-Thr-Cys-Cys-Gly-Xaa₃-Xaa₃-Gly-Asp-Trp-Gln-Cys-Val-Xaa₂-Ala, wherein Xaa₁ is 6-bromo-L-tryptophan, Xaa₂ is Gla or Glu and Xaa₃ is Hyp or Pro (SEQ ID NO:9).

16. The bromo-tryptophan conopeptide of claim 3 having an amino acid sequence selected from the group consisting of:
   (a) Thr-Arg-Thr-Cys-Gly-Gly-Xaa₁-Lys-Cys-Thr-Gly-Thr-Cys-Thr-Cys-Thr-Asn-Ser-Ser-Lys-Cys-Gly-Cys-Arg-Tyr-Asn-Val-His-Pro-Ser-Gly-Xaa₂-Gly-Cys-Gly-Cys-Ala-Cys-Ser, wherein Xaa₁ is Hyp or Pro and Xaa₂ is 6-bromo-L-tryptophan (SEQ ID NO:11); and
   (b) Gly-Gly-Xaa₁-Lys-Cys-Thr-Gly-Thr-Cys-Thr-Cys-Thr-Asn-Ser-Ser-Lys-Cys-Gly-Cys-Arg-Tyr-Asn-Val-His-Pro-Ser-Gly-Xaa₂-Gly-Cys-Gly-Cys-Ala-Cys-Ser, wherein Xaa₁ is Hyp or Pro and Xaa₂ is 6-bromo-L-tryptophan (SEQ ID NO:12).

* * * * *

UNITED STATES PATENT AND TRADEMARK OFFICE
CERTIFICATE OF CORRECTION

PATENT NO. : 5,889,147

DATED : 30 March 1999

INVENTOR(S) : Lourdes J. CRUZ et al.

It is certified that error appears in the above-identified patent and that said Letters Patent are hereby corrected as shown below:

<u>In the Claims</u>:
  Claim 6, column 55, line 46, "claim 3" should be --claim 5--.
  Claim 12, column 56, line 5, "claim 9" should be --claim 11--.

Signed and Sealed this

Twentieth Day of June, 2000

Attest:

Q. TODD DICKINSON

*Attesting Officer*  *Director of Patents and Trademarks*

SEQUENCE LISTING ( 1 ) GENERAL INFORMATION:

( i i i ) NUMBER OF SEQUENCES: 29

( 2 ) INFORMATION FOR SEQ ID NO:1:

( i ) SEQUENCE CHARACTERISTICS:
        ( A ) LENGTH: 8 amino acids
        ( B ) TYPE: amino acid
        ( C ) STRANDEDNESS:
        ( D ) TOPOLOGY: linear ( i i ) MOLECULE TYPE: protein ( i i i ) HYPOTHETICAL: NO ( v i ) ORIGINAL SOURCE:
        ( A ) ORGANISM: Conus radiatus ( i x ) FEATURE:
        ( A ) NAME/KEY: Modified-site
        ( B ) LOCATION: 3
        ( D ) OTHER INFORMATION: /note= "Xaa at residue 3 may be Hyp or Pro"

( i x ) FEATURE:
        ( A ) NAME/KEY: Modified-site
        ( B ) LOCATION: 7
        ( D ) OTHER INFORMATION: /note= "Xaa at residue 7 is 6-bromo-L- Trp"

( i x ) FEATURE:
        ( A ) NAME/KEY: Modified-site
        ( B ) LOCATION: 4
        ( D ) OTHER INFORMATION: /note= "Xaa at residue 4 is D-Trp"

( x i ) SEQUENCE DESCRIPTION: SEQ ID NO:1:

Gly Cys Xaa Xaa Glu Pro Xaa Cys
    1                          5

( 2 ) INFORMATION FOR SEQ ID NO:2:

( i ) SEQUENCE CHARACTERISTICS:
        ( A ) LENGTH: 7 amino acids
        ( B ) TYPE: amino acid
        ( C ) STRANDEDNESS:
        ( D ) TOPOLOGY: linear ( i i ) MOLECULE TYPE: protein ( i i i ) HYPOTHETICAL: NO ( v i ) ORIGINAL SOURCE:
        ( A ) ORGANISM: Conus imperalis ( i x ) FEATURE:
        ( A ) NAME/KEY: Modified-site
        ( B ) LOCATION: 1
        ( D ) OTHER INFORMATION: /note= "Xaa at residue 1 may be gamma- carboxyglutamate or Glu"

( i x ) FEATURE:
        ( A ) NAME/KEY: Modified-site ( B ) LOCATION: 6
( D ) OTHER INFORMATION: /note= "Xaa at residue 6 is
6-bromo-L- Trp"

( x i ) SEQUENCE DESCRIPTION: SEQ ID NO:2:

Xaa Cys Gly Gln Ala Xaa Cys
1               5

( 2 ) INFORMATION FOR SEQ ID NO:3:

( i ) SEQUENCE CHARACTERISTICS:
( A ) LENGTH: 33 amino acids
( B ) TYPE: amino acid
( C ) STRANDEDNESS:
( D ) TOPOLOGY: linear ( i i ) MOLECULE TYPE: protein ( i i i ) HYPOTHETICAL: NO ( v i ) ORIGINAL SOURCE:
( A ) ORGANISM: Conus radiatus ( i x ) FEATURE:
( A ) NAME/KEY: Modified-site
( B ) LOCATION: 1
( D ) OTHER INFORMATION: /note= "Xaa at residue 1 is
6-bromo-L- Trp"

( i x ) FEATURE:
( A ) NAME/KEY: Modified-site
( B ) LOCATION: 6..9
( D ) OTHER INFORMATION: /note= "Xaa at residues 6, 8 and 9
may be gamma- carboxyglutamate or Glu"

( i x ) FEATURE:
( A ) NAME/KEY: Modified-site
( B ) LOCATION: 21..22
( D ) OTHER INFORMATION: /note= "Xaa at residues 21 and 22
may be Hyp or Pro"

( i x ) FEATURE:
( A ) NAME/KEY: Modified-site
( B ) LOCATION: 29
( D ) OTHER INFORMATION: /note= "Xaa at residue 29 may be
gamma- carboxyglutamate or Glu"

( x i ) SEQUENCE DESCRIPTION: SEQ ID NO:3:

Xaa Ala Thr Ile Asp Xaa Cys Xaa Xaa Thr Cys Asn Val Thr Phe Lys
1               5                       10                      15

Thr Cys Cys Gly Xaa Xaa Gly Asp Trp Gln Cys Val Xaa Ala Cys Pro
        20                  25                  30

Val ( 2 ) INFORMATION FOR SEQ ID NO:4:

( i ) SEQUENCE CHARACTERISTICS:
( A ) LENGTH: 11 amino acids
( B ) TYPE: amino acid
( C ) STRANDEDNESS:
( D ) TOPOLOGY: linear ( i i ) MOLECULE TYPE: peptide ( i i i ) HYPOTHETICAL: NO ( v ) FRAGMENT TYPE: N-terminal ( v i ) ORIGINAL SOURCE:
( A ) ORGANISM: Conus radiatus ( i x ) FEATURE:
( A ) NAME/KEY: Modified-site
( B ) LOCATION: 1

( D ) OTHER INFORMATION: /note= "Xaa at residue 1 is
6-bromo-L- Trp"

( i x ) FEATURE:
( A ) NAME/KEY: Modified-site
( B ) LOCATION: 6..9
( D ) OTHER INFORMATION: /note= "Xaa at residues 6, 8 and 9
may be gamma- carboxyglutamate or Glu"

( x i ) SEQUENCE DESCRIPTION: SEQ ID NO:4:

Xaa  Ala  Thr  Ile  Asp  Xaa  Cys  Xaa  Xaa  Thr  Cys
1                   5                        10

( 2 ) INFORMATION FOR SEQ ID NO:5:

( i ) SEQUENCE CHARACTERISTICS:
( A ) LENGTH: 18 amino acids
( B ) TYPE: amino acid
( C ) STRANDEDNESS:
( D ) TOPOLOGY: linear ( i i ) MOLECULE TYPE: peptide ( i i i ) HYPOTHETICAL: NO ( v ) FRAGMENT TYPE: N-terminal ( v i ) ORIGINAL SOURCE:
( A ) ORGANISM: Conus radiatus ( i x ) FEATURE:
( A ) NAME/KEY: Modified-site
( B ) LOCATION: 1
( D ) OTHER INFORMATION: /note= "Xaa at residue 1 is
6-bromo-L- Trp"

( i x ) FEATURE:
( A ) NAME/KEY: Modified-site
( B ) LOCATION: 6..9
( D ) OTHER INFORMATION: /note= "Xaa at residues 6, 8 and 9
may be gamma- carboxyglutamate or Glu"

( x i ) SEQUENCE DESCRIPTION: SEQ ID NO:5:

Xaa  Ala  Thr  Ile  Asp  Xaa  Cys  Xaa  Xaa  Thr  Cys  Asn  Val  Thr  Phe  Lys
1                   5                        10                       15

Thr  Cys ( 2 ) INFORMATION FOR SEQ ID NO:6:

( i ) SEQUENCE CHARACTERISTICS:
( A ) LENGTH: 20 amino acids
( B ) TYPE: amino acid
( C ) STRANDEDNESS:
( D ) TOPOLOGY: linear ( i i ) MOLECULE TYPE: peptide ( i i i ) HYPOTHETICAL: NO ( v ) FRAGMENT TYPE: N-terminal ( v i ) ORIGINAL SOURCE:
( A ) ORGANISM: Conus radiatus ( i x ) FEATURE:
( A ) NAME/KEY: Modified-site
( B ) LOCATION: 1
( D ) OTHER INFORMATION: /note= "Xaa at residue 1 is
6-bromo-L- Trp"

( i x ) FEATURE:
( A ) NAME/KEY: Modified-site
( B ) LOCATION: 6..9
( D ) OTHER INFORMATION: /note= "Xaa at residues 6, 8 and 9
may be gamma- carboxyglutamate or Glu"

( x i ) SEQUENCE DESCRIPTION: SEQ ID NO:6:

Xaa Ala Thr Ile Asp Xaa Cys Xaa Xaa Thr Cys Asn Val Thr Phe Lys
1               5                   10                  15

Thr Cys Cys Gly
            20

( 2 ) INFORMATION FOR SEQ ID NO:7:

( i ) SEQUENCE CHARACTERISTICS:
        ( A ) LENGTH: 24 amino acids
        ( B ) TYPE: amino acid
        ( C ) STRANDEDNESS:
        ( D ) TOPOLOGY: linear ( i i ) MOLECULE TYPE: peptide ( i i i ) HYPOTHETICAL: NO ( v ) FRAGMENT TYPE: N-terminal ( v i ) ORIGINAL SOURCE:
        ( A ) ORGANISM: Conus radiatus ( i x ) FEATURE:
        ( A ) NAME/KEY: Modified-site
        ( B ) LOCATION: 1
        ( D ) OTHER INFORMATION: /note= "Xaa at residue 1 is
            6-bromo-L- Trp"

( i x ) FEATURE:
        ( A ) NAME/KEY: Modified-site
        ( B ) LOCATION: 6..9
        ( D ) OTHER INFORMATION: /note= "Xaa at residues 6, 8 and 9
            may be gamma- carboxyglutamate or Glu"

( i x ) FEATURE:
        ( A ) NAME/KEY: Modified-site
        ( B ) LOCATION: 21..22
        ( D ) OTHER INFORMATION: /note= "Xaa at residues 21 and 22
            may by Hyp or Pro"

( x i ) SEQUENCE DESCRIPTION: SEQ ID NO:7:

Xaa Ala Thr Ile Asp Asp Xaa Cys Xaa Xaa Thr Cys Asn Val Thr Phe
1               5                   10                  15

Lys Thr Cys Cys Gly Xaa Xaa Gly
                20

( 2 ) INFORMATION FOR SEQ ID NO:8:

( i ) SEQUENCE CHARACTERISTICS:
        ( A ) LENGTH: 27 amino acids
        ( B ) TYPE: amino acid
        ( C ) STRANDEDNESS:
        ( D ) TOPOLOGY: linear ( i i ) MOLECULE TYPE: peptide ( i i i ) HYPOTHETICAL: NO ( v ) FRAGMENT TYPE: N-terminal ( v i ) ORIGINAL SOURCE:
        ( A ) ORGANISM: Conus radiatus ( i x ) FEATURE:
        ( A ) NAME/KEY: Modified-site
        ( B ) LOCATION: 1
        ( D ) OTHER INFORMATION: /note= "Xaa at residue 1 is
            6-bromo-L- Trp"

( i x ) FEATURE:
        ( A ) NAME/KEY: Modified-site
        ( B ) LOCATION: 6..9

(D) OTHER INFORMATION: /note= "Xaa at residues 6, 8 and 9
may be gamma- carboxyglutamate or Glu"

(ix) FEATURE:
 (A) NAME/KEY: Modified-site
 (B) LOCATION: 21..22
 (D) OTHER INFORMATION: /note= "Xaa at residues 21 and 22
may be Hyp or Pro"

(xi) SEQUENCE DESCRIPTION: SEQ ID NO:8:

| Xaa | Ala | Thr | Ile | Asp | Xaa | Cys | Xaa | Xaa | Thr | Cys | Asn | Val | Thr | Phe | Lys |
|---|---|---|---|---|---|---|---|---|---|---|---|---|---|---|---|
| 1 | | | | 5 | | | | | 10 | | | | | | 15 |

| Thr | Cys | Cys | Gly | Xaa | Xaa | Gly | Asp | Trp | Gln | Cys |
|---|---|---|---|---|---|---|---|---|---|---|
| | | | 20 | | | | | 25 | | |

(2) INFORMATION FOR SEQ ID NO:9:

(i) SEQUENCE CHARACTERISTICS:
  (A) LENGTH: 30 amino acids
  (B) TYPE: amino acid
  (C) STRANDEDNESS:
  (D) TOPOLOGY: linear (ii) MOLECULE TYPE: peptide (iii) HYPOTHETICAL: NO (v) FRAGMENT TYPE: N-terminal (vi) ORIGINAL SOURCE:
  (A) ORGANISM: Conus radiatus (ix) FEATURE:
  (A) NAME/KEY: Modified-site
  (B) LOCATION: 1
  (D) OTHER INFORMATION: /note= "Xaa at residue 1 is
6-bromo-L- Trp"

(ix) FEATURE:
  (A) NAME/KEY: Modified-site
  (B) LOCATION: 6..9
  (D) OTHER INFORMATION: /note= "Xaa at residues 6, 8 and 9
may be gamma- carboxyglutamate or Glu"

(ix) FEATURE:
  (A) NAME/KEY: Modified-site
  (B) LOCATION: 21..22
  (D) OTHER INFORMATION: /note= "Xaa at residues 21 and 22
may be Hyp or Pro"

(ix) FEATURE:
  (A) NAME/KEY: Modified-site
  (B) LOCATION: 29
  (D) OTHER INFORMATION: /note= "Xaa at residue 29 may be
gamma- carboxyglutamate or Glu"

(xi) SEQUENCE DESCRIPTION: SEQ ID NO:9:

| Xaa | Ala | Thr | Ile | Asp | Xaa | Cys | Xaa | Xaa | Thr | Cys | Asn | Val | Thr | Phe | Lys |
|---|---|---|---|---|---|---|---|---|---|---|---|---|---|---|---|
| 1 | | | | 5 | | | | | 10 | | | | | | 15 |

| Thr | Cys | Cys | Gly | Xaa | Xaa | Gly | Asp | Trp | Gln | Cys | Val | Xaa | Ala |
|---|---|---|---|---|---|---|---|---|---|---|---|---|---|
| | | | 20 | | | | | 25 | | | | | 30 |

(2) INFORMATION FOR SEQ ID NO:10:

(i) SEQUENCE CHARACTERISTICS:
  (A) LENGTH: 41 amino acids
  (B) TYPE: amino acid
  (C) STRANDEDNESS:
  (D) TOPOLOGY: linear (ii) MOLECULE TYPE: protein (iii) HYPOTHETICAL: NO ( v i ) ORIGINAL SOURCE:
  ( A ) ORGANISM: Conus geographus ( i x ) FEATURE:
  ( A ) NAME/KEY: Modified-site
  ( B ) LOCATION: 9
  ( D ) OTHER INFORMATION: /note= "Xaa at residue 9 is Hyp or Pro"

( i x ) FEATURE:
  ( A ) NAME/KEY: Modified-site
  ( B ) LOCATION: 34
  ( D ) OTHER INFORMATION: /note= "Xaa at residue 34 is 6-bromo-L- Trp"

( x i ) SEQUENCE DESCRIPTION: SEQ ID NO:10:

| Gly | Cys | Thr | Arg | Thr | Cys | Gly | Gly | Xaa | Lys | Cys | Thr | Gly | Thr | Cys | Thr |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Cys | Thr | Asn | Ser | Ser | Lys | Cys | Gly | Cys | Arg | Tyr | Asn | Val | His | Pro | Ser |
|     |     |     | 20  |     |     |     |     | 25  |     |     |     |     | 30  |     |     |

| Gly | Xaa | Gly | Cys | Gly | Cys | Ala | Cys | Ser |
|     |     | 35  |     |     |     |     | 40  |     |

( 2 ) INFORMATION FOR SEQ ID NO:11:

( i ) SEQUENCE CHARACTERISTICS:
    ( A ) LENGTH: 39 amino acids
    ( B ) TYPE: amino acid
    ( C ) STRANDEDNESS:
    ( D ) TOPOLOGY: linear ( i i ) MOLECULE TYPE: protein ( i i i ) HYPOTHETICAL: NO ( v i ) ORIGINAL SOURCE:
    ( A ) ORGANISM: Conus geographus ( i x ) FEATURE:
    ( A ) NAME/KEY: Modified-site
    ( B ) LOCATION: 7
    ( D ) OTHER INFORMATION: /note= "Xaa at residue 7 is Hyp or Pro"

( i x ) FEATURE:
    ( A ) NAME/KEY: Modified-site
    ( B ) LOCATION: 32
    ( D ) OTHER INFORMATION: /note= "Xaa at residue 32 is 6-bromo-L- Trp"

( x i ) SEQUENCE DESCRIPTION: SEQ ID NO:11:

| Thr | Arg | Thr | Cys | Gly | Gly | Xaa | Lys | Cys | Thr | Gly | Thr | Cys | Thr | Cys | Thr |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Asn | Ser | Ser | Lys | Cys | Gly | Cys | Arg | Tyr | Asn | Val | His | Pro | Ser | Gly | Xaa |
|     |     |     | 20  |     |     |     |     | 25  |     |     |     |     | 30  |     |     |

| Gly | Cys | Gly | Cys | Ala | Cys | Ser |
|     |     | 35  |     |     |     |     |

( 2 ) INFORMATION FOR SEQ ID NO:12:

( i ) SEQUENCE CHARACTERISTICS:
    ( A ) LENGTH: 35 amino acids
    ( B ) TYPE: amino acid
    ( C ) STRANDEDNESS:
    ( D ) TOPOLOGY: linear ( i i ) MOLECULE TYPE: protein ( i i i ) HYPOTHETICAL: NO ( v i ) ORIGINAL SOURCE:
    ( A ) ORGANISM: Conus geographus ( i x ) FEATURE:
    ( A ) NAME/KEY: Modified-site
    ( B ) LOCATION: 3
    ( D ) OTHER INFORMATION: /note= "Xaa at residue 3 is Hyp or
        Pro"

( i x ) FEATURE:
    ( A ) NAME/KEY: Modified-site
    ( B ) LOCATION: 28
    ( D ) OTHER INFORMATION: /note= "Xaa at residue 28 is
        6-brom-L-Trp"

( x i ) SEQUENCE DESCRIPTION: SEQ ID NO:12:

Gly Gly Xaa Lys Cys Thr Gly Thr Cys Thr Cys Thr Asn Ser Ser Lys
1               5                   10                  15
Cys Gly Cys Arg Tyr Asn Val His Pro Ser Gly Xaa Gly Cys Gly Cys
                20                  25                  30
Ala Cys Ser
         35

( 2 ) INFORMATION FOR SEQ ID NO:13:

( i ) SEQUENCE CHARACTERISTICS:
        ( A ) LENGTH: 8 amino acids
        ( B ) TYPE: amino acid
        ( C ) STRANDEDNESS:
        ( D ) TOPOLOGY: linear ( i i ) MOLECULE TYPE: protein ( i i i ) HYPOTHETICAL: NO ( i x ) FEATURE:
        ( A ) NAME/KEY: Modified-site
        ( B ) LOCATION: 3
        ( D ) OTHER INFORMATION: /note= "Xaa at residue 3 is Hyp"

( i x ) FEATURE:
        ( A ) NAME/KEY: Modified-site
        ( B ) LOCATION: 4
        ( D ) OTHER INFORMATION: /note= "Xaa at residue 4 is D-Trp"

( i x ) FEATURE:
        ( A ) NAME/KEY: Modified-site
        ( B ) LOCATION: 7
        ( D ) OTHER INFORMATION: /note= "Xaa at residue 7 is
            6-bromo-D,L-Trp"

( x i ) SEQUENCE DESCRIPTION: SEQ ID NO:13:

Gly Cys Xaa Xaa Glu Pro Xaa Cys
1               5

( 2 ) INFORMATION FOR SEQ ID NO:14:

( i ) SEQUENCE CHARACTERISTICS:
        ( A ) LENGTH: 8 amino acids
        ( B ) TYPE: amino acid
        ( C ) STRANDEDNESS:
        ( D ) TOPOLOGY: linear ( i i ) MOLECULE TYPE: protein ( i i i ) HYPOTHETICAL: NO ( i x ) FEATURE:
        ( A ) NAME/KEY: Modified-site
        ( B ) LOCATION: 3
        ( D ) OTHER INFORMATION: /note= "Xaa at residue 3 is Hyp"

( i x ) FEATURE:
        ( A ) NAME/KEY: Modified-site
        ( B ) LOCATION: 7
        ( D ) OTHER INFORMATION: /note= "Xaa at residue 7 is 6-bromo-D,L- Trp"

(xi) SEQUENCE DESCRIPTION: SEQ ID NO:14:

```
Gly  Cys  Xaa  Trp  Glu  Pro  Xaa  Cys
1                  5
```

(2) INFORMATION FOR SEQ ID NO:15:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: protein (iii) HYPOTHETICAL: NO (ix) FEATURE:
        (A) NAME/KEY: Modified-site
        (B) LOCATION: 3
        (D) OTHER INFORMATION: /note= "Xaa at residue 3 is Hyp"

(ix) FEATURE:
        (A) NAME/KEY: Modified-site
        (B) LOCATION: 4
        (D) OTHER INFORMATION: /note= "Xaa at residue 4 is D-Trp"

(ix) FEATURE:
        (A) NAME/KEY: Modified-site
        (B) LOCATION: 7
        (D) OTHER INFORMATION: /note= "Xaa at residue 7 is
        6-bromo-D- Trp"

(xi) SEQUENCE DESCRIPTION: SEQ ID NO:15:

```
Gly  Cys  Xaa  Xaa  Glu  Pro  Xaa  Cys
1                  5
```

(2) INFORMATION FOR SEQ ID NO:16:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (iii) HYPOTHETICAL: YES (iv) ANTI-SENSE: NO (xi) SEQUENCE DESCRIPTION: SEQ ID NO:16:

CCRCACCANG GYTCCCA 17

(2) INFORMATION FOR SEQ ID NO:17:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:17:

GTTGTGTGGA ATTGTGAGCG GA 22

(2) INFORMATION FOR SEQ ID NO:18:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: protein (iii) HYPOTHETICAL: NO (vi) ORIGINAL SOURCE:
        (A) ORGANISM: Conus radiatus (ix) FEATURE:
        (A) NAME/KEY: Modified-site
        (B) LOCATION: 3
        (D) OTHER INFORMATION: /note= "Xaa at residue 3 is Hyp"

(ix) FEATURE:
        (A) NAME/KEY: Modified-site
        (B) LOCATION: 4
        (D) OTHER INFORMATION: /note= "Xaa at residue 4 is D-Trp"

(ix) FEATURE:
        (A) NAME/KEY: Modified-site
        (B) LOCATION: 7
        (D) OTHER INFORMATION: /note= "Xaa at residue 7 was blank from sequencing"

(xi) SEQUENCE DESCRIPTION: SEQ ID NO:18:

```
Gly  Cys  Xaa  Xaa  Glu  Pro  Xaa  Cys
 1                   5
```

(2) INFORMATION FOR SEQ ID NO:19:

(i) SEQUENCE CHARACTERISTICS:
        (A) LENGTH: 192 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Conus radiatus (ix) FEATURE:
        (A) NAME/KEY: CDS
        (B) LOCATION: 1..189

(xi) SEQUENCE DESCRIPTION: SEQ ID NO:19:

```
ATG  GGG  AAA  CTG  ACA  ATA  CTG  GTT  CTT  GTT  GCT  GCT  GTC  CTG  TTG  TCG        48
Met  Gly  Lys  Leu  Thr  Ile  Leu  Val  Leu  Val  Ala  Ala  Val  Leu  Leu  Ser
 1                   5                        10                       15

GCC  CAG  GTC  ATG  GTT  CAA  GGT  GAC  GGA  GAT  CAA  CCT  GCA  GAT  CGT  AAT        96
Ala  Gln  Val  Met  Val  Gln  Gly  Asp  Gly  Asp  Gln  Pro  Ala  Asp  Arg  Asn
                     20                        25                       30

GCA  GTG  CCA  AGA  GAC  GAT  AAC  CCA  GGT  GGA  GCG  AGT  GGA  AAG  TTC  ATG       144
Ala  Val  Pro  Arg  Asp  Asp  Asn  Pro  Gly  Gly  Ala  Ser  Gly  Lys  Phe  Met
                35                        40                       45

AAT  GTT  CTA  CGT  CGG  TCT  GGA  TGT  CCG  TGG  GAA  CCT  TGG  TGT  GGC            189
Asn  Val  Leu  Arg  Arg  Ser  Gly  Cys  Pro  Trp  Glu  Pro  Trp  Cys  Gly
            50                        55                       60

TGA                                                                                    192
```

(2) INFORMATION FOR SEQ ID NO:20:

( i ) SEQUENCE CHARACTERISTICS:
 ( A ) LENGTH: 63 amino acids
 ( B ) TYPE: amino acid
 ( D ) TOPOLOGY: linear ( i i ) MOLECULE TYPE: protein ( x i ) SEQUENCE DESCRIPTION: SEQ ID NO:20:

| Met | Gly | Lys | Leu | Thr | Ile | Leu | Val | Leu | Val | Ala | Ala | Val | Leu | Leu | Ser |
|---|---|---|---|---|---|---|---|---|---|---|---|---|---|---|---|
| 1 | | | | 5 | | | | | 10 | | | | | 15 | |
| Ala | Gln | Val | Met | Val | Gln | Gly | Asp | Gly | Asp | Gln | Pro | Ala | Asp | Arg | Asn |
| | | | 20 | | | | | 25 | | | | | 30 | | |
| Ala | Val | Pro | Arg | Asp | Asp | Asn | Pro | Gly | Gly | Ala | Ser | Gly | Lys | Phe | Met |
| | | | 35 | | | | 40 | | | | | 45 | | | |
| Asn | Val | Leu | Arg | Arg | Ser | Gly | Cys | Pro | Trp | Glu | Pro | Trp | Cys | Gly | |
| | 50 | | | | | 55 | | | | | 60 | | | | |

( 2 ) INFORMATION FOR SEQ ID NO:21:

( i ) SEQUENCE CHARACTERISTICS:
  ( A ) LENGTH: 5 amino acids
  ( B ) TYPE: amino acid
  ( C ) STRANDEDNESS:
  ( D ) TOPOLOGY: linear ( i i ) MOLECULE TYPE: peptide ( i i i ) HYPOTHETICAL: NO ( v ) FRAGMENT TYPE: internal ( i x ) FEATURE:
  ( A ) NAME/KEY: Modified-site
  ( B ) LOCATION: 3
  ( D ) OTHER INFORMATION: /note= "Xaa at residue 3 may be Leu
     or Ile"

( x i ) SEQUENCE DESCRIPTION: SEQ ID NO:21:

| Asn | Val | Xaa | Arg | Arg |
|---|---|---|---|---|
| 1 | | | | 5 |

( 2 ) INFORMATION FOR SEQ ID NO:22:

( i ) SEQUENCE CHARACTERISTICS:
  ( A ) LENGTH: 4 amino acids
  ( B ) TYPE: amino acid
  ( C ) STRANDEDNESS:
  ( D ) TOPOLOGY: linear ( i i ) MOLECULE TYPE: peptide ( i i i ) HYPOTHETICAL: NO ( v ) FRAGMENT TYPE: N-terminal ( v i ) ORIGINAL SOURCE:
  ( A ) ORGANISM: Conus radiatus ( i x ) FEATURE:
  ( A ) NAME/KEY: Modified-site
  ( B ) LOCATION: 1
  ( D ) OTHER INFORMATION: /note= "Xaa at residue 1 is
     bromo-Trp"

( x i ) SEQUENCE DESCRIPTION: SEQ ID NO:22:

| Xaa | Ala | Thr | Ile |
|---|---|---|---|
| 1 | | | |

( 2 ) INFORMATION FOR SEQ ID NO:23:

( i ) SEQUENCE CHARACTERISTICS:
  ( A ) LENGTH: 6 amino acids
  ( B ) TYPE: amino acid
  ( C ) STRANDEDNESS:
  ( D ) TOPOLOGY: linear ( i i ) MOLECULE TYPE: peptide ( i i i ) HYPOTHETICAL: NO ( v ) FRAGMENT TYPE: C-terminal ( v i ) ORIGINAL SOURCE:
  ( A ) ORGANISM: Conus imperialis ( i x ) FEATURE:
  ( A ) NAME/KEY: Modified-site
  ( B ) LOCATION: 5
  ( D ) OTHER INFORMATION: /note= "Xaa at residue 5 was blank
    in sequencing"

( x i ) SEQUENCE DESCRIPTION: SEQ ID NO:23:

Cys Gly Gln Ala Xaa Cys
1         5

( 2 ) INFORMATION FOR SEQ ID NO:24:

( i ) SEQUENCE CHARACTERISTICS:
  ( A ) LENGTH: 6 amino acids
  ( B ) TYPE: amino acid
  ( C ) STRANDEDNESS:
  ( D ) TOPOLOGY: linear ( i i ) MOLECULE TYPE: peptide ( i i i ) HYPOTHETICAL: NO ( v ) FRAGMENT TYPE: N-terminal ( v i ) ORIGINAL SOURCE:
  ( A ) ORGANISM: Conus imperialis ( i x ) FEATURE:
  ( A ) NAME/KEY: Modified-site
  ( B ) LOCATION: 1
  ( D ) OTHER INFORMATION: /note= "Xaa at residue 1 is
    gamma- carboxyglutamate"

( i x ) FEATURE:
  ( A ) NAME/KEY: Modified-site
  ( B ) LOCATION: 6
  ( D ) OTHER INFORMATION: /note= "Xaa at residue 6 is
    bromo-Trp"

( i x ) FEATURE:
  ( A ) NAME/KEY: Modified-site
  ( B ) LOCATION: 2
  ( D ) OTHER INFORMATION: /note= "Cys at residue 2 is
    modified with Cam"

( x i ) SEQUENCE DESCRIPTION: SEQ ID NO:24:

Xaa Cys Gly Gln Ala Xaa
1         5

( 2 ) INFORMATION FOR SEQ ID NO:25:

( i ) SEQUENCE CHARACTERISTICS:
  ( A ) LENGTH: 4 amino acids
  ( B ) TYPE: amino acid
  ( C ) STRANDEDNESS:
  ( D ) TOPOLOGY: linear ( i i ) MOLECULE TYPE: peptide ( i i i ) HYPOTHETICAL: NO (v) FRAGMENT TYPE: N-terminal (vi) ORIGINAL SOURCE:
    (A) ORGANISM: Conus radiatus (ix) FEATURE:
    (A) NAME/KEY: Modified-site
    (B) LOCATION: 1
    (D) OTHER INFORMATION: /note= "Xaa at residue 1 was blank from sequencing"

(xi) SEQUENCE DESCRIPTION: SEQ ID NO:25:

Xaa Ala Thr Ile
1

(2) INFORMATION FOR SEQ ID NO:26:

(i) SEQUENCE CHARACTERISTICS:
    (A) LENGTH: 19 amino acids
    (B) TYPE: amino acid
    (C) STRANDEDNESS:
    (D) TOPOLOGY: linear (ii) MOLECULE TYPE: peptide (iii) HYPOTHETICAL: NO (v) FRAGMENT TYPE: internal (vi) ORIGINAL SOURCE:
    (A) ORGANISM: Conus radiatus (ix) FEATURE:
    (A) NAME/KEY: Modified-site
    (B) LOCATION: 2..5
    (D) OTHER INFORMATION: /note= "Xaa at residues 2, 4 and 5 were blank from sequencing"

(ix) FEATURE:
    (A) NAME/KEY: Modified-site
    (B) LOCATION: 17..18
    (D) OTHER INFORMATION: /note= "Xaa at residues 17 and 18 are Hyp"

(xi) SEQUENCE DESCRIPTION: SEQ ID NO:26:

Asp Xaa Cys Xaa Xaa Thr Cys Asn Val Thr Phe Lys Thr Cys Cys Gly
1               5                   10                  15

Xaa Xaa Gly (2) INFORMATION FOR SEQ ID NO:27:

(i) SEQUENCE CHARACTERISTICS:
    (A) LENGTH: 10 amino acids
    (B) TYPE: amino acid
    (C) STRANDEDNESS:
    (D) TOPOLOGY: linear (ii) MOLECULE TYPE: peptide (iii) HYPOTHETICAL: NO (v) FRAGMENT TYPE: C-terminal (vi) ORIGINAL SOURCE:
    (A) ORGANISM: Conus radiatus (ix) FEATURE:
    (A) NAME/KEY: Modified-site
    (B) LOCATION: 6
    (D) OTHER INFORMATION: /note= "Xaa at residue 6 was blank from sequencing"

(xi) SEQUENCE DESCRIPTION: SEQ ID NO:27:

Asp Trp Gln Cys Val Xaa Ala Cys Pro Val (2) INFORMATION FOR SEQ ID NO:28:

(i) SEQUENCE CHARACTERISTICS:
        (A) LENGTH: 237 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Conus radiatus (ix) FEATURE:
        (A) NAME/KEY: CDS
        (B) LOCATION: 1..234

(xi) SEQUENCE DESCRIPTION: SEQ ID NO:28:

```
ATG TCG GGA TTG GGA TTC ATG GTG CTA ACC CTT CTA CTT CTT ACG TTC         48
Met Ser Gly Leu Gly Phe Met Val Leu Thr Leu Leu Leu Leu Thr Phe
 65                   70                      75

ATC GCA ACC AGT CAT CAG GAT AGA GGA GAG AAG CAG GCG ACG CAA AGG         96
Ile Ala Thr Ser His Gln Asp Arg Gly Glu Lys Gln Ala Thr Gln Arg
 80                   85                      90                  95

CAC GCA ATC AAT GTC ATA AGG AGA AGA TTA ATC ACT CGC TGG GCA ACA        144
His Ala Ile Asn Val Ile Arg Arg Arg Leu Ile Thr Arg Trp Ala Thr
                     100                    105                 110

ATT GAC GAG TGC GAA GAG ACA TGC AAC GTG ACG TTT AAG ACC TGC TGC        192
Ile Asp Glu Cys Glu Glu Thr Cys Asn Val Thr Phe Lys Thr Cys Cys
                115                    120                 125

GGT CCA CCT GGA GAT TGG CAA TGT GTC GAA GCA GTC CCC GTG                234
Gly Pro Pro Gly Asp Trp Gln Cys Val Glu Ala Val Pro Val
            130                    135                 140

TAG                                                                    237
```

(2) INFORMATION FOR SEQ ID NO:29:

(i) SEQUENCE CHARACTERISTICS:
        (A) LENGTH: 78 amino acids
        (B) TYPE: amino acid
        (D) TOPOLOGY: linear (ii) MOLECULE TYPE: protein (xi) SEQUENCE DESCRIPTION: SEQ ID NO:29:

```
Met Ser Gly Leu Gly Phe Met Val Leu Thr Leu Leu Leu Leu Thr Phe
 1               5                   10                  15

Ile Ala Thr Ser His Gln Asp Arg Gly Glu Lys Gln Ala Thr Gln Arg
            20                  25                  30

His Ala Ile Asn Val Ile Arg Arg Arg Leu Ile Thr Arg Trp Ala Thr
            35                  40                  45

Ile Asp Glu Cys Glu Glu Thr Cys Asn Val Thr Phe Lys Thr Cys Cys
        50                  55                  60

Gly Pro Pro Gly Asp Trp Gln Cys Val Glu Ala Val Pro Val
 65                  70                  75
```